(12) United States Patent
Habu et al.

(10) Patent No.: US 7,592,502 B2
(45) Date of Patent: Sep. 22, 2009

(54) KNOCK-IN NON-HUMAN ANIMAL PRODUCING HUMAN TISSUE FACTOR

(75) Inventors: Kiyoshi Habu, Gotenba (JP); Kou-ichi Jishage, Gotenba (JP); Hideki Adachi, Gotenba (JP); Naohiro Yabuta, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 341 days.

(21) Appl. No.: 10/478,058

(22) PCT Filed: May 17, 2002

(86) PCT No.: PCT/JP02/04818

§ 371 (c)(1),
(2), (4) Date: Nov. 18, 2003

(87) PCT Pub. No.: WO02/094016

PCT Pub. Date: Nov. 28, 2002

(65) Prior Publication Data

US 2004/0244063 A1 Dec. 2, 2004

(30) Foreign Application Priority Data

May 18, 2001 (JP) .............. 2001-149712
Aug. 8, 2001 (JP) .............. 2001-241218
Sep. 27, 2001 (JP) .............. 2001-297947
Nov. 19, 2001 (JP) .............. 2001-353765

(51) Int. Cl.
*A01K 67/027* (2006.01)
*C12N 15/00* (2006.01)
*C12N 15/87* (2006.01)
*C12N 5/00* (2006.01)
*C12N 5/02* (2006.01)

(52) U.S. Cl. .............. 800/18; 800/21; 800/25; 435/455; 435/463; 435/320.1; 435/325

(58) Field of Classification Search .............. 800/3, 800/8, 9, 13, 14, 18, 21, 22, 25; 435/455, 435/463, 320.1, 325
See application file for complete search history.

(56) References Cited

FOREIGN PATENT DOCUMENTS

CA 2 388 408 A1 4/2001

OTHER PUBLICATIONS

Erlich et al. PNAS, 96: 8138-8143 (Jul. 1999).*
Kappell et al. Current Opinion in Biotechnology 3:548-553 (1992).*
Mullins et al. Hypertension 22:630-633 (1993).*
Houdebine. J. Biotech. 34:269-287 (1994).*
Mullins et al. J. Clin. Invest. 97:1557-1560 (1996).*
Cameron. Molec. Biol. 7:253-265 (1997).*
Sigmund. Arterioscler. Throm. Vasc. Biol. 20:1425-1429 (2000).*
Niemann. Transg. Res. 7:73-75 (1998).*
Moreadith et al. J. of Mol. Med. 75:208-216 (1997).*
Pera et al. Journal of Cell Science 113: 5-10 (2000).*
Holschneider et al. Int J. Devl. Neuroscience 18:615-618, 2000.d.*
Mackman et al. Biochemistry, 28: 1755-1762, 1989.*
Gerlai. Trends Neurosci., 19:177-181 (1996).*
Lariviere et al., J. of Pharmacology and Exp. Therapeutics,297:467-473 (2001).*
Barthold. Genetica, 122:75-88 (2004).*
Pearson. Nature, 415: 8-9, Jan. 2002.*
Seong. Trends in Genetica, 20(2): 59-62, 2004.*
Graham C.N. Parry et al., "Low Levels of Tissue Factor Are Compatible with Development and Hemostasis in Mice", The Journal of Clinical Investigation, Feb. 1998, pp. 560-569, vol. 101-No. 3.
Jonathan Erlich et al., "Tissue factor is required for uterine hemostasis and maintenance of the placental labyrinth during gestation", Proc. Natl., Acad, Sci. USA, Jul. 1999, pp. 8138-8143, vol. 96.
Thomas N. Sato, "Gene Trap, Gene Knockout, Gene Knock-In, and Transgenics in Vascular Development", Thrombosis and Haemostasis, Aug. 1999, pp. 865-869, vol. 82-No. 2.
Nigel Mackman et al., "Structure of the Murine Tissue Factor Gene", Arteriosclerosis and Thrombosis, Apr. 1992, pp. 474-483, vol. 12-No. 4.
Paul J. Declerck et al., "Generation of Monoclonal Antibodies against Autologous Proteins in Gene-inactivated Mice", The Journal of Biological Chemistry, Apr. 1995, pp. 8397-8400, vol. 270-No. 15.
Graham C.N. Parry et al., "Mouse embryogenesis requires the tissue factor extracellular domain but not the cytoplasmic domain", The Journal of Clinical Investigation, Jun. 2000, pp. 1547-1554, vol. 105-No. 11.
Bromberg, Michael E. et al., "Role of Tissue Factor in Metastasis: Functions of the Cytoplasmic and Extracellular Domains of the Molecule", Thrombosis and Haemostasis, vol. 82, 1999, pp. 88-92.
Melis, Els et al., "Thrombophilia in mice expressing a tissue factor variant lacking its transmembrane and cytosolic domain", Biochemical and Biophysical Research Communications, vol. 333, No. 2, Jul. 29, 2005, pp. 488-495.
Taylor, F. B. et al., "Lethal *E. coli* Septic Shock is Prevented by Blocking Tissue Factor With Monoclonal Antibody", Circulatory Shock, vol. 33, No. 3, 1991, pp. 127-134.

\* cited by examiner

*Primary Examiner*—Thaian N Ton
(74) *Attorney, Agent, or Firm*—Foley & Lardner LLP

(57) ABSTRACT

A non-human animal that produces human tissue factor (TF) without substantially producing non-human animal tissue factor, said animal having a genome in which cDNA encoding human TF has been inserted upstream of the translation initiation codon for the non-human animal genomic TF gene.

3 Claims, 12 Drawing Sheets

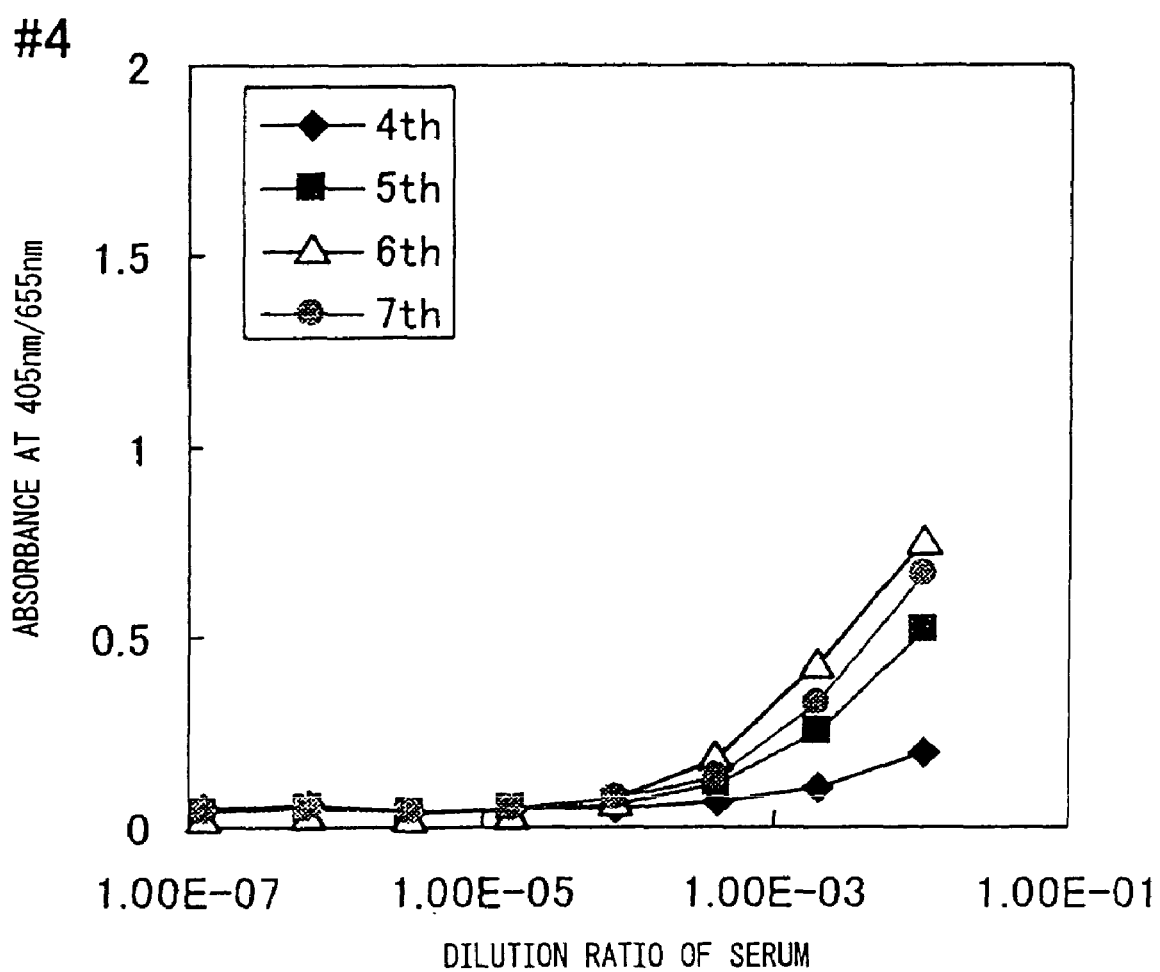

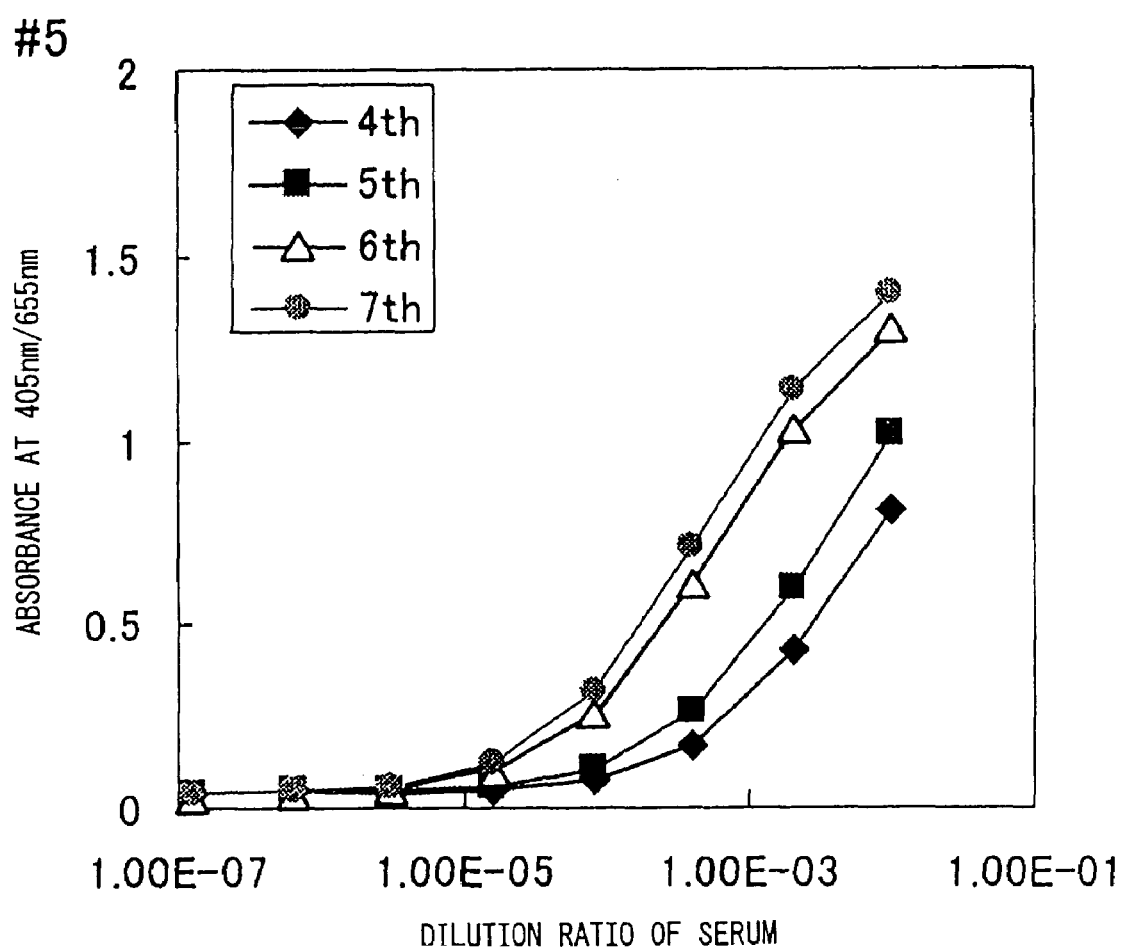

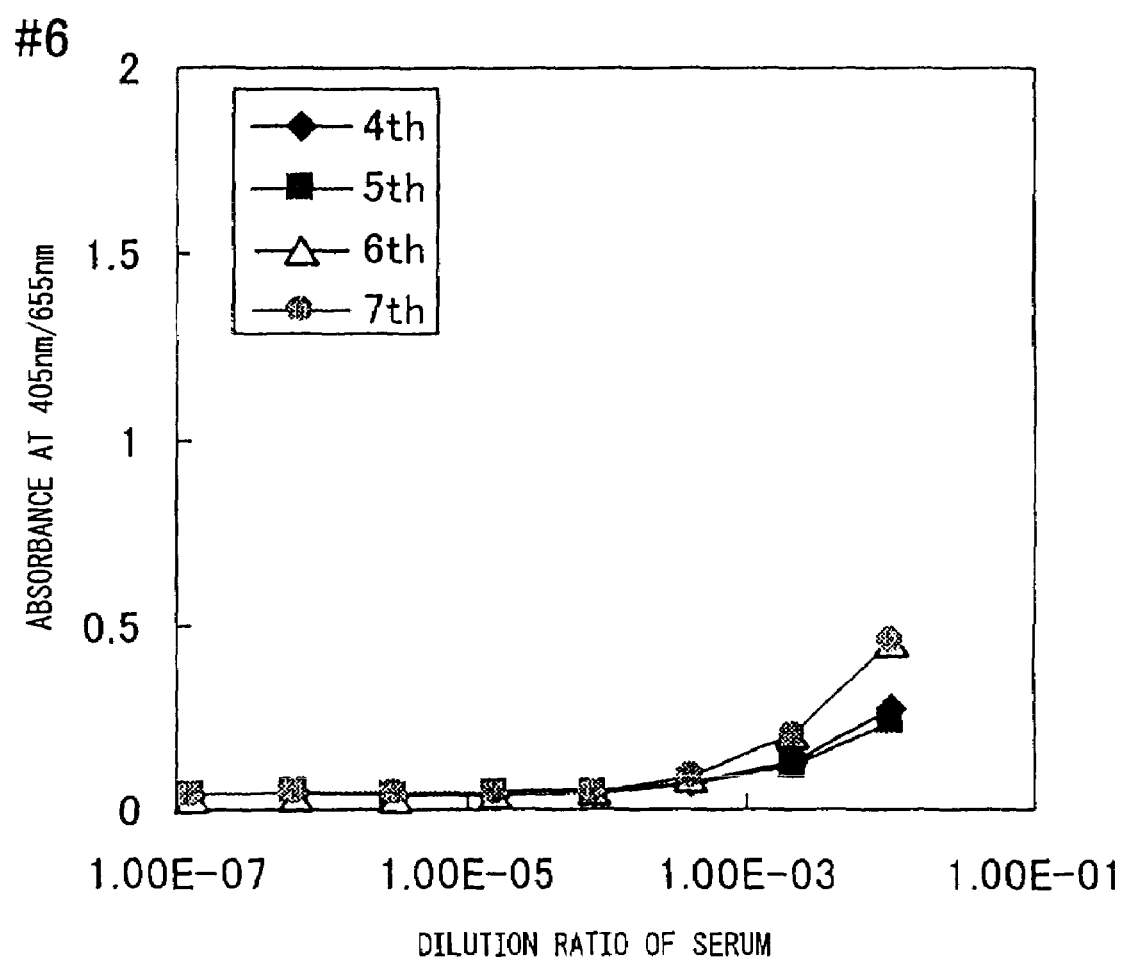

KNOCK-IN NON-HUMAN ANIMAL PRODUCING HUMAN TISSUE FACTOR

FIELD OF THE INVENTION

The present invention relates to knock-in non-human animals that produce human tissue factor (hTF).

BACKGROUND ART

Inhibiting agents of tissue factor (TF) are useful as inhibitors of blood coagulation, inhibitors of angiogenesis, therapeutic agents for arteriosclerosis, and the like. However, inhibiting agents of human tissue factor are highly species-specific, and, for example, anti-human TF antibody does not react to tissue factors from animals other than primates. Therefore, the creation of animals that express human TF is highly desired for the evaluation of inhibiting agents of human TF.

Though a knock-out mouse for human TF exhibits embryonic lethality, the expression of human TF can circumvent embryonic lethality (Parry G C N et al., J. Clin. Invest. 101: 560-569 (1998)). However, as this mouse has an introduced human TF minigene, the expression of tissue factor is low and thus breeding performance is poor (Erlich J. et al., Proc. Natl. Acad. Sci. USA 96:8138-8143 (1999)).

DISCLOSURE OF THE INVENTION

Thus, the present invention is intended to provide a non-human animal that can produce human TF.

In order to solve the above problem, the present invention provides a non-human animal that produces human TF without substantially producing non-human animal tissue factor. More specifically, the present invention provides a non-human animal which has a genome wherein a human TF-encoding gene has been inserted. Preferably, the human TF-encoding gene has been inserted onto the same chromosome as that for non-human animal TF gene. Preferably, the human TF-encoding gene has been inserted upstream of the translation initiation codon for non-human animal TF gene. Preferably, the human TF-encoding gene comprises an AU-rich response element (ARE) or a polyA additional signal at the 3'-end thereof. More preferably, the human TF-encoding gene comprises an AU-rich response element (ARE) and a polyA additional signal at the 3'-end thereof. Preferably, the non-human animal is a rodent, for example a mouse.

The present invention also provides various methods for using the above-mentioned knock-in non-human animal.

Thus, the present invention provides a method of screening a therapeutic agent for a disease caused by human TF, said method comprising:

(a) administering a test substance to a knock-in non-human animal that produces the human TF of the present invention or a non-human animal obtained by mating said non-human animal with another non-human animal; and (b) determining whether or not the symptom of the disease caused by human TF has been suppressed in the non-human animal that received said test substance.

For example, said disease caused by human TF is thrombosis or sepsis.

The present invention also provides a method of confirming whether or not a test substance is safe, said method comprising:

(a) administering a test substance to a knock-in non-human animal that produces the human TF of the present invention or a non-human animal obtained by mating said non-human animal with another non-human animal; and (b) confirming whether or not the non-human animal that received said test substance develops a bleeding symptom.

The present invention also provides a method of screening an anti-tumor agent, said method comprising:

(a) administering a test substance to a knock-in non-human animal that produces the human TF of the present invention or a non-human animal obtained by mating said non-human animal with another non-human animal; and (c) determining whether or not tumor has been suppressed in the non-human animal that received said test substance.

The present invention also provides a method of screening an angiogenesis-inhibiting agent, said method comprising:

(a) administering a test substance to a knock-in non-human animal that produces the human TF of the present invention or a non-human animal obtained by mating said non-human animal with another non-human animal; and (c) determining whether or not angiogenesis has been suppressed in the non-human animal that received said test substance.

The present invention also provides a method of screening a therapeutic agent for arteriosclerosis, said method comprising:

(a) administering a test substance to a knock-in non-human animal that produces the human TF of the present invention or a non-human animal obtained by mating said non-human animal with another non-human animal; and (b) determining whether or not arteriosclerosis has been suppressed in the non-human animal that received said test substance.

The present invention also provides a method of preparing anti-TF antibody against non-human animal TF, said method comprising immunizing the above non-human animal with tissue factor derived from said non-human animal.

BRIEF EXPLANATION OF THE DRAWINGS

FIG. 10 is a graph similar to FIG. 7 showing the result of the 76 line mouse No. 4.

FIG. 11 is a graph similar to FIG. 7 showing the result of the 76 line mouse No. 5.

FIG. 12 is a graph similar to FIG. 7 showing the result of the 76 line mouse No. 6.

BEST MODE FOR CARRYING OUT THE INVENTION

Figure 1:
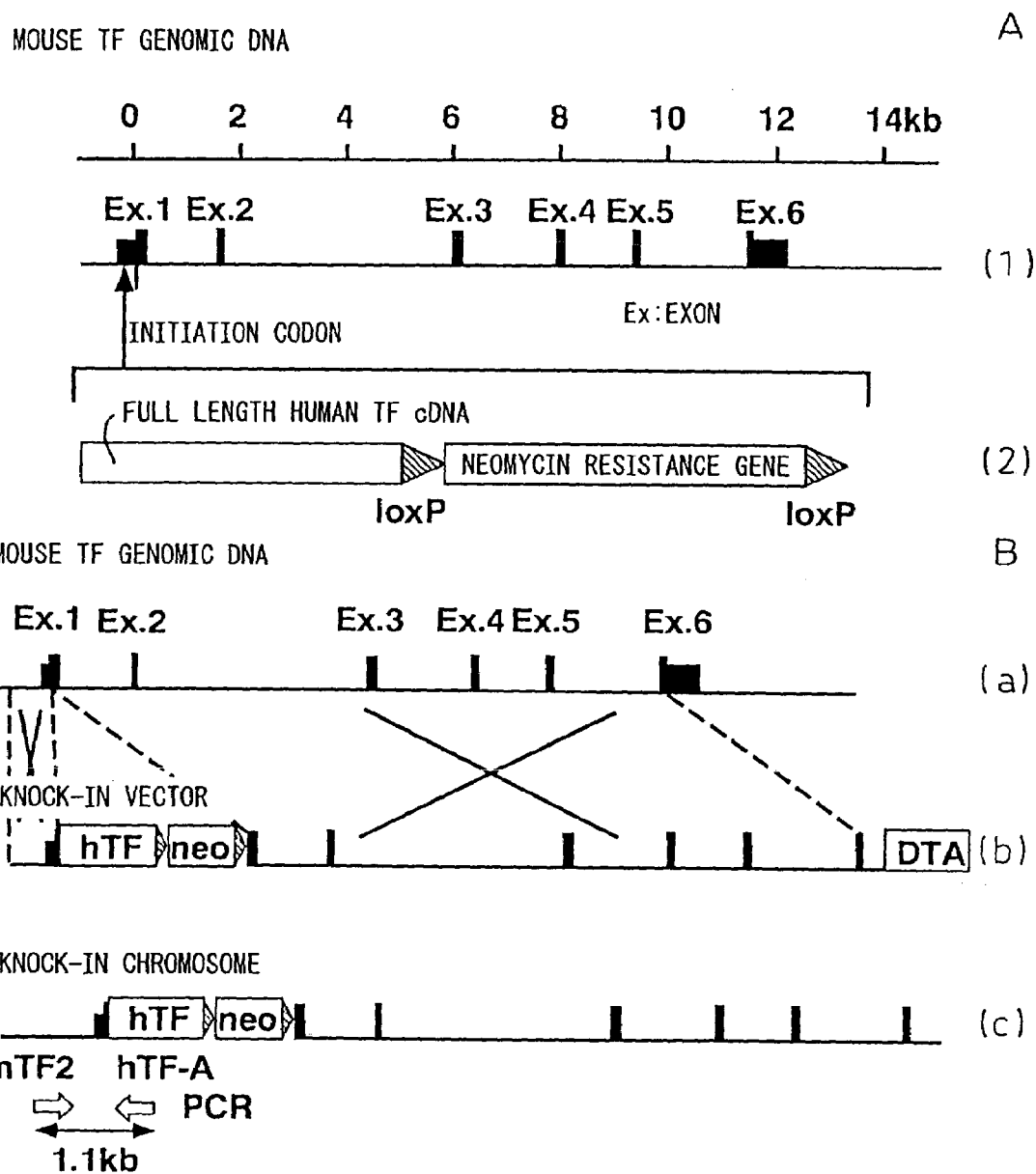
FIG. 1 is a drawing that schematically illustrates the formation of genomic DNA in the creation of a human tissue factor (TF) knock-in mouse. In the figure, A schematically illustrates the relation of a mouse TF genomic DNA (1) and a full-length human TF cDNA and the neomycin-resistant gene to be inserted (2). B is a drawing that schematically illustrates how a mouse TF genomic DNA (a) and a knock-in vector (b) undergo homologous recombination to form a knock-in genomic DNA (c), wherein the x mark between (a) and (b) indicates that homologous recombination takes place between (a) and (b).

In order to produce human TF in non-human animals, a gene encoding human TF may be inserted into a suitable site in the genome of the non-human animals (transgenic non-human animals). However, if it is desired to obtain non-human animals that satisfy the two requirements of not producing non-human animal TF and of producing human TF, it is necessary to inactivate the native TF gene of the non-human animals. On the other hand, since it is known from Parry et al., J. Clin. Invest. 101:560 (1998) that there is a regulatory element for expression in intron 1 between exon 1 and exon 2 of TF, the non-human animal TF genomic gene was not deleted, but the method of inactivating the expression of the non-human animal TF gene was adopted.

Thus, according to the present invention, as a site into which the human TF-encoding gene is to be inserted, the site on the same chromosome as that for the genomic gene of the non-human animal TF, specifically upstream of the translation initiation codon of the genomic gene of the non-human animal TF is preferable. By this approach, it is expected that human TF gene only is expressed and no TF gene of the non-human animals is expressed based on a biological rule that the first initiation codon is preferentially used when a plurality of initiation codons occur in series. Furthermore, the presence of a polyA additional signal at the 3'-end of human TF cDNA would prevent read through of the genomic gene of the non-human animal TF.

Human TF of the present invention may be the human TF having the full-length amino acid sequence or fragments (preferably peptides of 100 or more amino acid residues, and more preferably peptides of 200 or more amino acid residues, and for example a peptide containing 274 amino acids of amino acid residues -32 to 242 as described in Morrissey et al., Cell 50:129-135 (1987)) of human TF, and preferably human TF having the full-length amino acid sequence. Thus, the gene encoding human TF is not specifically limited, and it may be a gene encoding the full-length human TF or a gene encoding a fragment thereof, and it may preferably be a gene encoding the full-length human TF.

The gene encoding human TF of the present invention is not specifically limited as long as it is a gene capable of expressing human TF and, for example, cDNA or genomic DNA may be used. According to the present invention, the preferred gene encoding human TF is cDNA. Furthermore, other genes such as regulatory genes that regulate the expression of gene encoding human TF of the present invention may be added to the said gene. The origin of regulatory genes that are added to human TF is not specifically limited, and the genes may be derived from humans or from non-human animals.

Furthermore, according to the present invention, an AU-rich response element (ARE), a polyA additional signal, an untranslated region (UTR) etc. may be added to the gene encoding human TF. As the AU-rich response element (ARE), sequences known to a person skilled in the art may be used, and for example ATTTA etc. may be used. As the polyA additional signal, sequences known to a person skilled in the art may be used, and for example AATAAA etc. may be used. As the untranslated region, there can be mentioned for example 3' UTR and 5' UTR, with 3' UTR being preferred. The origin of an AU-rich response element (ARE), a polyA additional signal, an untranslated region (UTR) etc. for use in the present invention is not specifically limited, and those derived from humans and from non-human animals may be used.

When an AU-rich response element (ARE), a polyA additional signal, an untranslated region or the like is added to the gene encoding human TF, one of them may be added, and preferably two or more of them are added (for example, an AU-rich response element (ARE) and a polyA additional signal, or an untranslated region and a polyA additional signal, etc.). Alternatively, when an AU-rich response element (ARE), a polyA additional signal, an untranslated region or the like is added, a plurality of the same species may be added (for example, when polyA additional signals are added, two or more of polyA additional signals of the same sequence or of different sequences may be added). Then, a vector containing the above structure may be introduced into ES cells in a standard method, and the ES cells are injected into non-human animal embryos to reproduce the non-human animal.

If the non-human animal TF is not substantially reproduced, it means that the expression of the non-human animal TF has been artificially suppressed and, preferably, the non-human animal TF cannot be detected. As methods of detecting non-human animal TF, for example, a detection method using the anti-TF antibody against non-human animal TF described in Example 2 may be mentioned.

The non-human animals of the present invention are not specifically limited, and rodents such as mice, rats and hamsters, non-human primates such as monkeys and chimpanzees, mammals such as sheep, cattle and pigs, avians, amphibians, reptiles, fish and the like may be used, and preferably rodents, and more preferably mice.

The knock-in non-human animals of the present invention can be used as animal models for diseases caused by human TF. Diseases caused by human TF include, for example, thrombosis (for example, disseminated intravascular coagulation syndrome; DIC), arterial stenosis and occlusion, cerebral infarction, venous thrombosis, pulmonary embolism, intraatrial thrombosis), sepsis caused by infection, etc. Furthermore, the knock-in non-human animals of the present invention can be used for the creation of disease model animals such as tumors, angiogenesis and arteriosclerosis in addition to the above diseases.

Thus, by using the knock-in non-human animals of the present invention as these disease models, therapeutic agents or preventive agents for these diseases can be screened.

For example, screening of therapeutic agents or preventive agents for diseases caused by human TF may be carried out by administering a test substance to a knock-in non-human animal of the present invention in which thrombosis was induced, and then determining whether or not the disease caused by human TF has been suppressed.

Furthermore, screening can also be done using non-human animals of the present invention that have been fed with a chow. For example, non-human animals obtained after a high fat diet may be used to screen drugs for arteriosclerosis. Furthermore, non-human animals obtained after transplanting a tumor to the non-human animals of the present invention may be used to screen anti-tumor agents or angiogenesis inhibitors.

In the screening method for angiogenesis inhibitors, non-human animals obtained by administering angiogenesis-inducing agents, such as FGF, VEGF and PDGF known to those skilled in the art, to the non-human animals of the present invention can be used.

In the screening method for therapeutic agents or preventive agents for sepsis, non-human animals can also be used in which sepsis was induced by administering bacteria or bacterial components to the non-human animals of the present invention or by extruding bacteria etc. occurring in the intestine of the non-human animals out of the intestine using a surgical method. As bacteria, there can be mentioned, for example, Gram negative bacteria such as *Neisseria meningitidis* and *Pseudomonas aeruginosa* etc. and Gram positive bacteria such as *staphylococci* and *Listeria*, but Gram negative bacteria are preferred. As preferred examples of bacterial components, there can be mentioned endotoxins present as a component of bacterial cell wall, and lipopolysaccharide (LPS), a component of endotoxins, may be used alone.

Furthermore, screening may be carried out using non-human animals obtained by crossing the knock-in non-human animals of the present invention with other non-human animals. Thus, according to the present invention, not only the cases that used the non-human animals of the present invention but also the cases that used non-human animals obtained by crossing the non-human animals of the present invention with other non-human animals are included in the screening method using the non-human animals of the present invention.

For example, in the case of mice, screening of anti-tumor agents or anti-angiogenesis inhibitors can be carried out using mice obtained by crossing the knock-in mice of the present invention with cancer-prone mice. As cancer-prone mice, those known to those skilled in the art can be used, and for example C3H mice, AKR mice, 129 mice and the like can be used. Furthermore, it is also possible to transplant a tumor to mice obtained by crossing with Severe Combined Immunodeficiency Disease (SCID) mice (Bosma G C et al., Nature 301:527-530 (1983);

available from CLEA Japan Inc.) or with nude mice and then to screen anti-tumor agents or anti-angiogenesis inhibitors.

Furthermore, it is also possible to screen anti-arteriosclerosis agents by using mice obtained by crossing the knock-in mice of the present invention with arteriosclerosis-prone mice (for example, apolipoprotein E (ApoE) knock-out mice (Piedrahita J A et al., Proc. Natl. Acad. Sci. USA 89:4471-4475 (1992); available from The Jackson Laboratory (USA), LDLR knock-out mice). Even when screening is carried out using mice obtained as described above, it is included in the screening method using mice of the present invention.

Test substances for use in screening are not specifically limited, and there can be mentioned, for example, peptides, proteins, non-peptide compounds, synthetic compounds, fermentation products, cell extracts and the like.

With respect to the screening method of the present invention, in addition to the knock-in non-human animals of the present invention and non-human animals obtained by crossing said knock-in non-human animals with other non-human animals, biological samples such as organs, tissues, cells, blood and the like harvested from these non-human animals may be used.

Whether or not diseases caused by human TF are suppressed can be judged, when the disease is disseminated intravascular coagulation syndrome (DIC), using as an index the Ministry of Health and Welfare DIC diagnostic criteria (revised in 1988), or the DIC scoring system (Taylor F B, Jr. et al., (2001) Thromb. Haemost. 86:1327-1330) etc. In the case of arterial stenosis and occlusion, it can be judged by the patency rate of the blood vessel or the presence or absence of restenosis; in the case of cerebral infarction, it can be judged by whether or not the formation of cerebral infarction foci has been suppressed in the middle cerebral artery occlusion model; in the case of sepsis, it can be judged by whether or not a mortality rate has been improved; in the case of venous thrombosis, it can be judged by whether or not the amount of thrombi has been reduced; in the case of pulmonary embolism, it can be judged by whether or not a mortality rate has been improved; in the case of intraatrial thrombosis, it can be judged by whether or not the amount of thrombi has been reduced.

Also, whether or not tumor growth or angiogenesis has been suppressed can be judged by the size or frequency of their formation, and whether or not arteriosclerosis has been suppressed can be judged on whether or not hyperplasia of neointima has been suppressed after non-invasive intravascular treatment.

As the non-human animals of the present invention have a characteristics that they do not produce non-human animal TF, they can be used for the preparation of anti-TF antibody against non-human animal TF. Anti-TF antibody against non-human animal TF can be prepared by immunizing the knock-in non-human animals of the present invention with non-human animal TF purified from the brain etc. of normal non-human animals, or recombinant non-human animal TF prepared by using hosts such as *Escherichia coli*, yeast, insect cells, mammalian cells, or partial peptide fragments of non-human animal TF (Declerck P J et al. (1995) J. Biol. Chem. 270:8397-8400: an example of method of preparing antibody by immunization into knock-out animals), or by injecting naked DNA that expresses non-human animal TF into the non-human animals of the present invention. Generation of antibody can be carried out according to a known standard method, in which polyclonal antibody (antiserum) or monoclonal antibody can be prepared.

Also, the non-human animal of the present invention can be used for the evaluation of safety (for example, evaluation of bleeding symptoms) etc. when therapeutic agents (for example, anti-human TF antibody or substances that bind to human TF), for diseases caused by human TF, were administered.

Furthermore, biological samples such as organs, tissues, cells and blood harvested from the non-human animals of the present invention may be used to prepare diagnostics or reagents derived from human TF. These diagnostics or reagents can be used not only for the diagnosis of diseases caused by human TF but also for the evaluation of therapeutic agents. For example, they may be used as reagents for determining prothrombin time by replacing human-derived thromboplastin reagents.

Now, the present invention will be explained more specifically below.

EXAMPLE 1

Establishment of Knock-In Mice (1) Construction of Vectors

The mouse TF (mTF) genomic gene was cloned by a PCR method with reference to a report by Mackman et al. (Arteriosclerosis and Thrombosis 12:474, 1992). An about 3 kb region of mTF from exon 1 to exon 2 was amplified with a primer set of mTF1SpS and mTF2A, and then cloned into the pGEM-T-Easy vector (Promega). The sequences of the primers are as follows: mTF1SpS: 5'-CGA GCA AAT GCT ACT AGT AGG ATA AGT GAT CGT CTA AGG C-3' (SEQ ID No. 1); MTF2A: 5'-CTG TAC AGT GTA GGT ATA GTT GGT GGG TTT GGG TTG-3' (SEQ ID No. 2).

The composition of the reaction mixture for the PCR method was: mouse genomic DNA (derived from ES cells, the 129 mice, 400 µg/ml), 1 µl; 10×LA buffer, 5 µl; dNTP, 8 µl; mTF1S pS (100 µM), 0.1 µl; mTF2A (100 µM), 0.1 µl; distilled water, 35.3 µl; LA Taq (TAKARA) enzyme, 0.5 µl. PCR comprised a preheating at 94° C. for 1 min, 30 cycles of amplification reaction of 98° C. for 20 seconds and 68° C. for 15 minutes, as well as heating at 72° C. for 10 minutes.

Also, an about 10.5 kb region from exon 2 to exon 6 of the mTF gene was cloned by a PCR method. The primer set used is as follows and the PCR condition was the same as above. mTF1SpS: 5'-CGA GCA AAT GCT ACT AGT AGG ATA AGT GAT CGT CTA AGG C-3' (SEQ ID No. 1); mTFe6ScA: 5'-ATC AGA GCT CTC CGC AAC AGT GCC GT-3' (SEQ ID No. 3). The fragment amplified was cleaved with a SacI restriction enzyme and cloned into pBluescript (STRATAGENE).

The 3'-UTR (regulatory region for expression) of human TF (hTF) cDNA was cloned from mRNA of J82 cells (human bladder cancer) using the following primers and BcaBEST RNA PCR kit (TAKARA). ShTF3: 5'-TGT TCA AGC AGT GAT TCC C-3' (SEQ ID No. 4); RhTF2: 5'-AAC AAT TCC CAG TCA CCT T-3' (SEQ ID No. 5).

The cloned 1.37 kb fragment, after confirming the sequence, was ligated to the coding sequence (CDS) of hTF at the HpaI site to construct the full-length hTF cDNA. Though the periphery of the initiation codon of the full-length hTF cDNA has been converted to the Kozak sequence, 3' UTR region, which is based on a report by Mackman et al. (Biochemistry 28:1755, 1989), includes a region up to the site where polyA has been added ( AATAAAGGTGACTGGGAATTGTT, the underlined part represents a polyA additional signal) (SEQ ID NO: 6).

The sequence is shown in SEQ ID NO: 7. In the sequence, bases No. 1-11 have been altered to the Kozak sequence (Nucleic Acids Research 15:8125, 1987), ATG of bases 12-14 is the translation initiation codon for human TF, and the coding region of human TF ends at base 896.

Using these mTF genomic DNA and the full-length hTF cDNA, a knock-in vector shown in FIG. 1 was constructed. Human TF (hTF) cDNA was inserted into the Kpn I site preceding the initiation codon (ATG) in exon 1 of mTF together with a drug resistance gene (neo). As Parry et al. have reported the presence of a regulatory element for expression in the intron (between exon 1 and exon 2) of the TF gene (J. Clin. Invest. 101:560, 1998), the procedure of deleting the genome of mTF was not carried out.

However, as this vector has hTF cDNA preceding the mTF gene and also has a polyA additional signal, this knock-in mouse was expected to express only the hTF gene. It was believed that even if hTF was read through, without added polyA, to transcribe the mTF gene, hTF is only translated from the fusion mRNA and mTF protein would not be produced based on a biological rule that the first initiation codon antecedes in the translation of protein.

Furthermore, since this vector has exon 2 of mTF in parallel in the construct, it was thought that, even if the protein of mTF is translated, it would not be functional. The gene of diphtheria toxin A fragment (DTA) is a negative selection marker to obtain homologous recombinant efficiently. Also, as the promoter of the pgk gene has been added to a drug resistance gene, neo, the neo gene is expressed in ES cells, and this portion suppresses the expression of the hTF gene that was introduced upstream, a procedure of extracting this portion (neo) was added. For this purpose, the neo gene was flanked by the loxP sequence (ATA ACT TCG TAT AGC ATA CAT TAT ACG AAG TTA T) (SEQ ID NO: 8), providing a mechanism such that, when Cre acts thereon, the resulting recombination will extract the intercalated neo gene.

(2) Introduction into ES Cells

Using the Mouse Kit (LEXIION GENETICS Inc.) commercially available from TAKARA, the above hTF knock-in (KI) vector was electroporated into ES cells (AB2.2 cells derived from 129 SvEv mice), and the homologous recombinants were screened by a PCR method. The vector (60 µg) was linearized with Not I, extracted with phenol/chloroform, precipitated with ethanol, and then dissolved in PBS for use.

ES cells used in screening were cultured in a 96-well plate, washed twice in 200 µl per well of the PBS solution, and then a cell lysis buffer of the following composition (10×LA buffer (for TAKARA LA Taq), 5 µl; 5% NP-40, 5 µl; proteinase K (TAKARA, 20 mg/ml), 4 µl; distilled water, 36 µl) was added thereto, which was treated at 55° C. for 2 hours, followed by a treatment at 95° C. for 15 minutes to inactivate proteinase K to provide a PCR sample.

The PCR reaction mixture comprised: the sample, 1 µl; 2×GC buffer, 25 µl; dNTP (2.5 mM), 8 µl; primer (20 µM each), 1 µl each; LA Taq (TAKARA), 0.5 µl; and distilled water, 13.5 µl (a total of 50 µl). The PCR condition comprised a preheating at 95° C. for 1 min, 40 cycles of amplification reaction of 95° C. for 30 seconds and 64° C. for 30 seconds and 72° C. for 1 minute 20 seconds, as well as heating at 72° C. for 10 minutes.

Primers are as described below. In samples of ES cells that underwent homologous recombination, an about 1.1 kb band is amplified. Primer mTF2 was placed in the mTF genomic region of the 5'-end outside of the KI vector, and hTF-A was placed inside of hTF cDNA (see FIG. 1). mTF2 (forward): 5'-CCA GTA GGA TAA GTG ATC GTC TAA GGC-3' (SEQ ID No. 9); hTF-A (reverse): 5'-GCC ACA GTA TTT GTA GTG CCT GAA GC-3' (SEQ ID No. 10).

The result of screening (efficiency of homologous recombination) is shown below. In the experiment, in two runs, 1,180 ES cells were analyzed to obtain a total of 13 clones that underwent homologous recombination (the efficiency of recombination was 1.1% on the average of two runs).

TABLE 1

| Run No. | No. of ES cells analyzed | No. of homologous recombinants | Efficiency of recombination |
|---|---|---|---|
| 1 | 484 | 8 | 1.70% |
| 2 | 696 | 5 | 0.70% |
| Total | 1180 | 13 | 1.10% |

(3) Establishment of Knock-In Mice

Homologous recombinant ES clones were suspended by trypsin treatment, and washed in the ES cell medium. At an interval of 48 hours, 5 IU of equine chorionic gonadotropin (eCG) and human chorionic gonadotropin (hCG) were intraperitoneally given to c57BL/6J female mice to induce superovulation, then they were mated with c57BL/6J male mice. The day when the plug of female mice was confirmed was regarded as day 0.5. On gestation day 2.5, the uterus and the oviduct were flushed, and the morula stage and 8 cell stage embryos were collected. The collected embryos were cultured overnight at 37° C. and were developed to the blastocyst stage. 10-15 ES cells were injected into these blastocystes. The embryos after injection were transplanted into the uterus of the pseudopregnancy recipient mice of the ICR at a gestation day 2.5, and the offspring were obtained 17 days later.

The following table is a summary of the result of injection. It is well known that the chimeras with a high proportion of ES-cell-derived coat color (having a high percentage of agouti color) are contributing to germ line. And if the XY (ES cells) contribution is high, the chimeras will typically develop as males. Thus, ES clones 7, 76, and 80 are expected to be mice capable of transmitting the KI allele.

TABLE 2

| Clone | No. of transferred embryos | No. of implanted embryos | (%) | No. of offsprings Total | (%) | ♂ | ♀ | No. of hair color chimera Total | (%) | ♂ | ♀ | Proportion of ES cell-derived coat color on male chimeras |
|---|---|---|---|---|---|---|---|---|---|---|---|---|
| 75 | 48 | 22 | 46% | 16 | 33% | 10 | 6 | 2 | 13% | 2 | 0 | 60, 20% |
| 7 | 94 | 73 | 78% | 31 | 33% | 22 | 9 | 13 | 42% | 10 | 3 | 90, 90, 90, 90, 90, 90, 70, 70, 70% |
| 1 | 32 | 22 | 69% | 2 | 6% | 1 | 1 | 0 | 0% | 0 | 0 | |
| 18 | 32 | 24 | 75% | 11 | 34% | 4 | 7 | 4 | 36% | 1 | 3 | 60% |
| 76 | 46 | 29 | 63% | 11 | 24% | 7 | 4 | 3 | 27% | 3 | 0 | 100%, 95%, 20% |
| 28 | 34 | 17 | 50% | 10 | 29% | 4 | 6 | 2 | 20% | 1 | 1 | 10% |
| 80 | 48 | 28 | 58% | 12 | 25% | 12 | 0 | 8 | 67% | 8 | 0 | 80, 80, 70, 50, 40, 30, 20, 5% |

Investigation of Germline Transmission

Since the mice derived from three ES clones that are homologous recombinants had favorable coat color chimeric rate, these chimeric mice were crossed with c57BL/6J female mice to investigate the germline transmission of the ES clone-derived chromosome. The following table summarizes the result.

generated by in vitro fertilization of mature c57BL/6J oocytes with hTF KI sperm. At this time, two vectors (pCAGGS-Cre-NLS and pCre-Pac) were used. pCAGGS-Cre-NLS is a pCAGGS vector in which the Cre gene has been inserted at the C-terminal end of which a nuclear transfer signal (NLS) is added.

TABLE 3

| Clone | Percentage of chimera | No. of births | Total No. of offsprings ♂ | Total No. of offsprings ♀ | Average No. of babies born | ES clone-derived mice ♂ | ES clone-derived mice ♀ | Percentage of germline |
|---|---|---|---|---|---|---|---|---|
| 7 | 90% | 5 | 13 | 14 | 5.4 | 12 | 11 | 85% |
| 7 | 90% | 4 | 19 | 11 | 7.5 | 16 | 9 | 83% |
| 7 | 90% | 3 | 10 | 19 | 9.7 | 0 | 0 | 0% |
| 7 | 90% | 6 | 14 | 19 | 5.5 | 13 | 18 | 94% |
| 7 | 90% | 0 | 0 | 0 | 0 | 0 | 0 | 0% |
| 7 | 90% | 5 | 10 | 22 | 6.4 | 3 | 13 | 50% |
|  |  |  |  | Total of ES clone-derived mice | | 44 | 51 |  |
| 76 | 100% | 2 | 4 | 5 | 4.5 | 2 | 1 | 33% |
| 76 | 95% | 5 | 10 | 16 | 5.2 | 0 | 3 | 12% |
|  |  |  |  | Total of ES clone-derived mice | | 2 | 4 |  |
| 80 | 80% | 1 | 2 | 3 | 5 | 0 | 0 | 0% |
| 80 | 80% | 0 | 0 | 0 | 0 | 0 | 0 | 0% |
| 80 | 70% | 4 | 14 | 16 | 7.5 | 0 | 0 | 0% |

Of six chimeric mice (all had a coat color chimeric rate of 90%) derived from clone 7, four chimeric mice showed efficient germline transmission, and a total of 95 F1 mice could be obtained. Although the chimeric mice derived from clone 80 did not exhibit germline transmission, chimeric mice derived from clone 76 showed germline transmission, and therefore two independent lines of knock-in mice were established. Here in below, mice derived from these clones are designated as the 07 line and the 76 line.

The pCAGGS vector is composed of the cytomegalovirus enhancer and the chicken β actin promoter, and it permits strong expression of the inserted gene in mammalian cells. On the other hand, pCre-Pac is a vector in which Cre to which NLS is added at the N-terminal end is derived by the promoter of MC-1. Using these vectors, a procedure of removing the neo gene was carried out. The following table summarizes the result.

TABLE 4

| Name of vector | No. of surviving eggs | No. of injected eggs | (%) | No. of transplantation | No. of offsprings | (%) | No. of hTF KI mouse | No. of neo deleted mouse | Efficiency |
|---|---|---|---|---|---|---|---|---|---|
| pCAGGS-Cre | 60 | 79 | 76% | 56 | 8 | 14% | 2 | 2 | 100% |
| pCre-Pac | 81 | 106 | 76% | 80 | 17 | 21% | 4 | 4 | 100% |

Gene Analysis of KI Mice

F1 mice can be judged based on coat color whether or not they are offspring (agouti color) derived from the ES clone or offspring (black) derived from the host embryo. However, even the offspring derived from the ES clone have a probability of ½ of having the chromosome of the side that actually underwent homologous recombination. In order to differentiate them, about 2 cm of the tail of the mice after ablactation was harvested, and genomic DNA was extracted by KURABO's NA-1000. Analysis was performed on 100 ng of the genomic DNA using a PCR method used in the above screening.

(4) Removal of the Neo Gene

In order to remove neo gene, the Cre expression vector (about 3 ng/μl) was injected into the pronucleus of eggs As described in the above table, in either of the vectors the efficiency of removing neo was equally 100%, but when Cre to which no NLS had been added was used, they were in a chimeric state in which neo was not completely extracted. The analysis was carried out using 5 μg of genomic DNA by a dot Southern blot method. Thus, it was found that the one for which the hTF gene was only detected using the neo gene and the hTF gene as probes was hTF KI mice in which neo has been removed, and the one for which detection was made with both probes was hTF KI mice in which neo could not be removed.

(5) Generation of hTF Homo Mice hTF KI mice (-neo) obtained in the above were crossed with each other to generate the homo mice (TF humanized mice) of hTF. In the gene analysis of these mice, the presence or absence of the hTFKI allele was determined using the above PCR method, and using the primer set [mTF-5 (forward) 5'-TTCACTCAAACCCACTGCGG-3' (SEQ ID No. 11); mTF-H (reverse) 5'-GCTACGCTACAGGAGCGATCG-3' (SEQ ID No. 12], the presence or absence of the wild type allele was determined. PCR conditions were the same, but PCR reactions were carried out separately. In the completely humanized homo TF KI mice, bands are amplified for PCR alone for determining the KI allele.

Expression Analysis of hTF Mice

Figure 2:
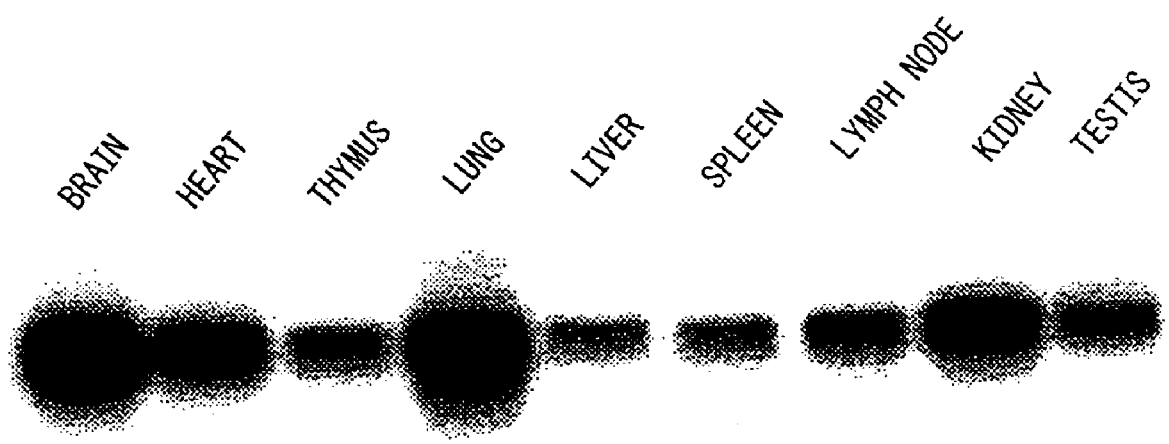
FIG. 2 is a drawing showing the result of Northern blot analysis that indicates the tissue distribution of TF gene expression in the mouse.
Figure 3:
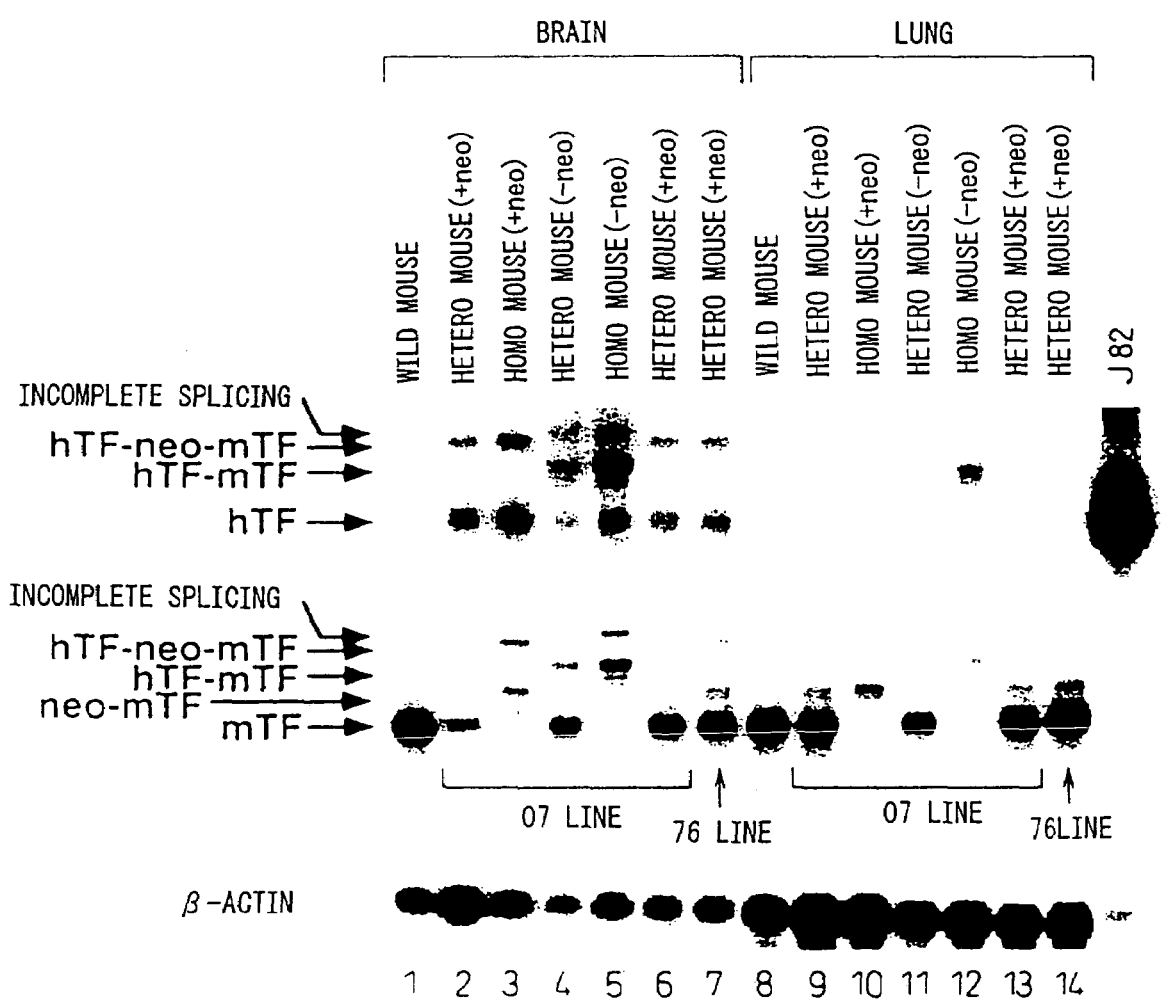
FIG. 3 is a drawing showing the result of Northern blot analysis that indicates the expression products of various mice related to the present invention.

Tissues that express mTF were investigated using the Northern blot method. The mice used were four 8 week-old C57BL/6J ♂ mice. polyA+ RNA was prepared from the brain, the lung, the thymus, the heart, the liver, the spleen, lymph nodes, the kidney, and the testis, and 5 µg of them were used for the experiment (FIG. 2). The expression of mTF was confirmed in each tissue, and among them, expression was highest in the brain and the lung. Therefore, the expression analysis of the prepared hTF KI mice was carried out on these tissues. The result is shown in FIG. 3.

The mice used are one month-old wild mice ♀ (+/+) (lanes 1 and 8) and the same one month-old 07 line female (lanes 2-5, and 9-12). Among them, for hetero mice (KI/+) (lanes 2, 4, 9 and 11), homo mice (KI/KI) (lanes 3, 5, 10, and 12), and those in which neo was further removed (−neo) (lanes 4, 5, 11 and 12), and those not removed (+neo) (lanes 2, 3, 9 and 10), the expression of mTF was compared in the brain (lanes 1-5) and the lung (lanes 8-12). Also, the expression of hTF was compared between the lines on 4 month-old hetero mice, ♀, of the 07 line (lanes 6 and 13) and the 76 line (7 and 14) and furthermore for the 07 line (lanes 2, 6, 9 and 13) the expression of hTF was compared between ages.

These data confirmed that the knock-in vector caused homologous recombination as designed giving mice that express hTF instead of mTF. Thus, the expression pattern of hTF in the established hTF KI mice is very similar to that of the original mTF suggesting that knock-in mice were successfully established. There was no difference of expression between the week-old ages or between the lines.

By crossing hTF KI mice (KI/KI, +neo) thus created with each other, propagative ability was examined. As a result, they exhibited a propagative ability of a similar degree to the wild type mice, and the problem reported by Erlich et al. (Proc. Natl. Acad. Sci. USA 96:8138, 1999) during gestation, that has been demonstrated in the double transgenic mice of the mTF knock-out mice and the hTF genome transgenic mice, was not observed in these mice.

TABLE 5

Performance of crossing in human TF knock-in mice

| Knock-in mouse | First birth | Second birth | Third birth |
| --- | --- | --- | --- |
| ♂ No. 147 × ♀ No. 115 | 1 ♀ 4 ♂ | 3 ♀ 4 ♂ | 4 ♀ 2 ♂ |
| ♂ No. 142 × ♀ No. 111 | 3 ♀ 4 ♂ | 5 ♀ 4 ♂ | 3 ♀ 7 ♂ |
| Wild type × Wild type | 1 ♀ 0 ♂ | 3 ♀ 1 ♂ | 3 ♀ 2 ♂ |
| Wild type × Wild type | 3 ♀ 4 ♂ | 5 ♀ 4 ♂ | 3 ♀ 7 ♂ |

EXAMPLE 2

Confirmation of TF Expression in Knock-In Mice (1) Extraction of TF Protein

Brain acetone powders were prepared from five each of male and female wild type mice C57BL/6J (CLEA Japan Inc.) and seven each of male and female 76 line human TF knock-in mice. After the cervical dislocation of the mice, craniotomy was performed to extract the whole brain, which was quickly frozen in liquid nitrogen. To one g weight of the brain, 2 ml of TBS (Tris-buffered-saline; Takara Shuzo) containing 1 mM PMSF (phenylmethylsulfonyl fluoride) was added, and the tissue was homogenized in a metal and Teflon homogenizer followed by centrifugation at 10,000×g, 4° C., for 1 hour to remove the supernatant.

TBS at an amount equal to the one described above was added to the precipitate, which was stirred well, and centrifuged at 10,000×g, 4° C., for 1 hour to remove the supernatant. To the precipitate obtained, 2 ml of ice-cold acetone per g of the brain was added and suspended well. After centrifuging at about 2,000×g, 4° C., for 20 minutes, the supernatant was discarded. This was repeated and defatted. To the precipitate obtained, nitrogen gas was injected to dryness, which was prepared as a brain acetone powder.

400 µl of TBS containing 2% Triton X-100 was added to 10 mg of the brain acetone powder from each of the wild type mice, male and female, and the human TF knock-in mice, male and female, which were then subjected to sonication for 1 hour to be suspended. After recovering the supernatant by centrifugation (4° C., 15,000 rpm, 10 minutes), 1.2 ml of TBS was added for dilution, and then 1M $MnCl_2$ and 1M $CaCl_2$ were added to a final concentration of 1 mM. The above extract was added to about 50 µl of the ConA Sepharose resin (Pharmacia Biotech) equilibrated with 0.5% Triton X-100/TBS (containing 1 mM $MnCl_2$ and 1 mM $CaCl_2$), and mixed by invention at 4° C. overnight.

The resin was washed in 10 resin volumes of 0.5% Triton X-100/TBS (containing 1 mM $MnCl_2$ and 1 mM $CaCl_2$), and eluted with the SDS-PAGE Sample Buffer (Bio-Rad Laboratories), treated at 95° C. for 5 minutes, and centrifuged (25° C., 15,000 rpm, 1 minute) to collect the supernatant, which was use as a sample. The CHO cell-derived soluble human TF (see WO99/51743) and CHO cell-derived soluble mouse TF were mixed with an equal amount of the SDS-PAGE Sample Buffer (Bio-Rad Laboratories) to prepare samples. Prestained Precision Protein Standards™ (Bio-Rad Laboratories) was used as the molecular weight marker.

(2) Detection of TF by Using Anti-TF Antibody

The extract from the brain acetone powder at 3 mg/lane equivalent and the purified soluble TF at 100 ng/lane were electrophoresed on two sheets of 10% polyacrylamide gel (Tefco). It was electrically transferred to the PVDF membrane (Millipore) in the Semidry type protting instrument, and protted in 1×PBS/Casein Blocker (Bio-Rad Laboratories). One (for human TF detection) was reacted with 2 µg/ml of anti-human TF antibody (American Diagnostica Inc., Cat. #4503), and the other (for mouse TF detection) was reacted with 2 µg/ml of anti-mouse TF antibody MFR-37 at room temperature for 1 hour.

Figure 4:
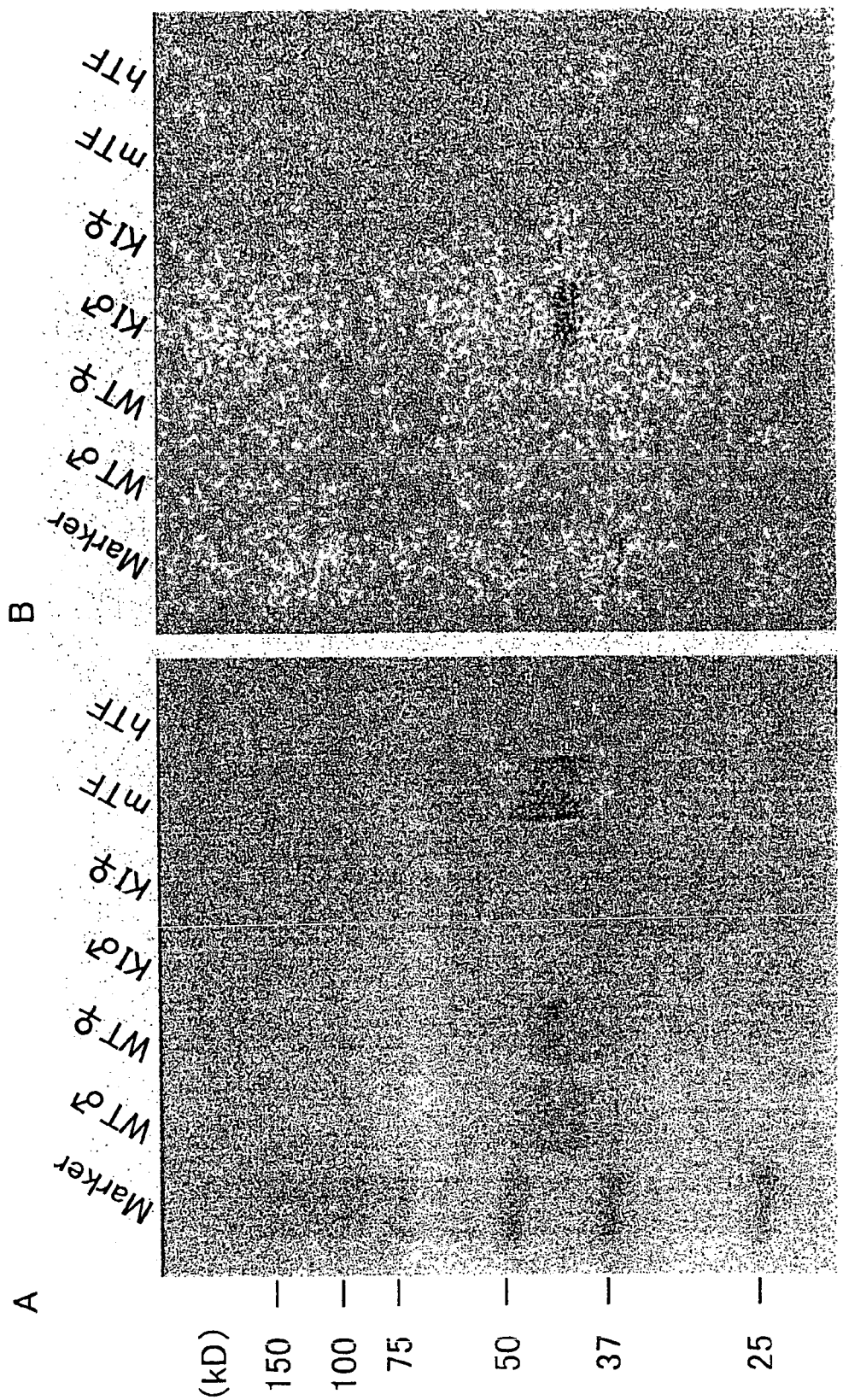
Referring to FIG. 4, the expression of TF in the brain of a wild-type mouse and a knock-in mouse was detected by (A) anti-mouse TF antibody MFR-37 and (B) anti-human TF antibody ADI#4503, and they are photographs showing the result of Western blot analysis.

After washing three times in PBS containing 0.05% Tween™ 20 for 5 minutes, a secondary antibody diluted 1000-fold was reacted. Using alkaline phosphatase-labelled goat anti-mouse IgG (H+L) (ZYMED, Cat. #62-6522) for the human TF detection system and alkaline phosphatase-labelled goat anti-rat Ig (BIOSOURCE, Cat. #ARI3405) for the mouse TF detection, reaction was conducted at room temperature for 1 hour. After washing three times in PBS containing 0.05% Tween™ 20 for 5 minutes, color was developed with 1st Step NBT/BCIP (PIERCE). The result is shown in FIG. 4. In FIG. 4, A represents a result of detection with anti-mouse TF antibody MFR-37, and B represents a result of detection with anti-human TF antibody ADI #4503. With anti-mouse TF antibody, TF was detected only in the brain tissue of the wild type mouse, and with anti-human TF antibody, TF was detected only in the brain tissue of the human TF knock-in mouse.

(3) Detection of Human TF Activity

Using the brain acetone powder prepared as above, human TF activity was detected based on plasma coagulation activity. Human plasma used was the standard human plasma (Dade Behring Marburg GmbH), and mouse plasma was citrate-added plasma taken from the ICR mouse. The brain acetone powder was suspended in TBS at 8 mg/ml, and mixed with equal amounts of 40, 4, 0.4, 0 μg/ml of humanized anti-human TF antibody hATR-5 (ib2) (WO99/51743) diluted in TBS, and reacted at room temperature for 1 hour. An acetone powder-antibody mixture (50 μl/cup) was added to 100 μl/cup of plasma, and incubated at 37° C. for 3 minutes. 20 mM $CaCl_2$ (Dade Behring Marburg GmbH) was added thereto to start coagulation, and coagulation time was measured using the Amelung KC-10A (Heinrich Amelung GmbH).

Figure 5:
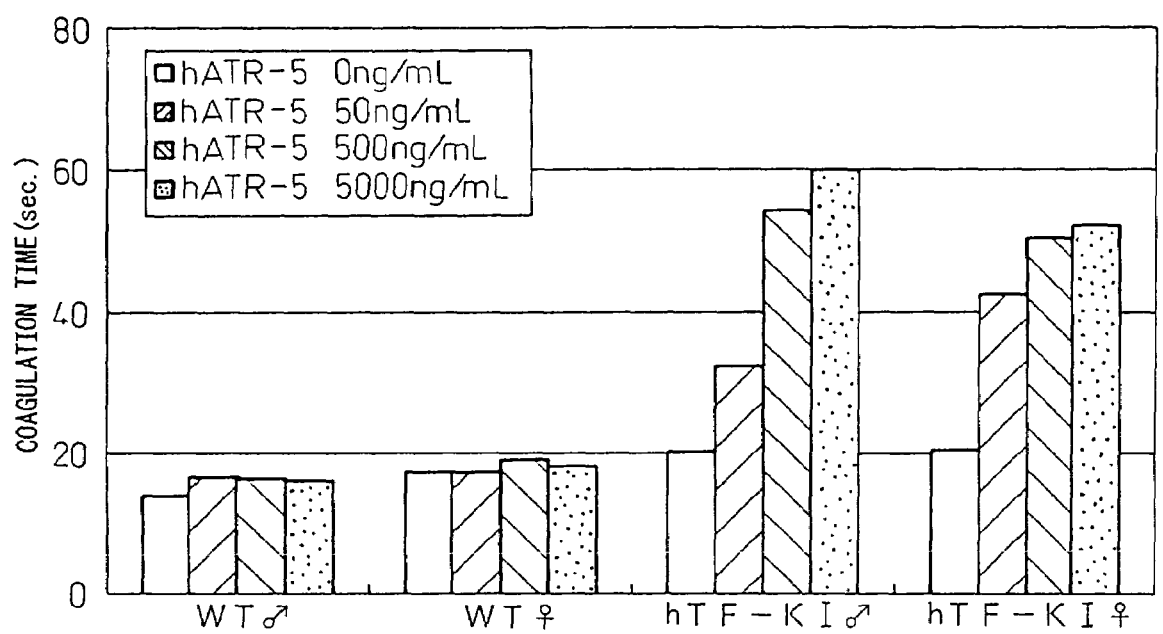
FIG. 5 is a graph showing a result in which the inhibition of mouse plasma coagulation by anti-human TF antibody in a wild type mouse and a human TF knock-in mouse was determined by measuring plasma coagulation time, wherein the y-axis represents the plasma coagulation time and each column represents the final concentration of antibody.
Figure 6:
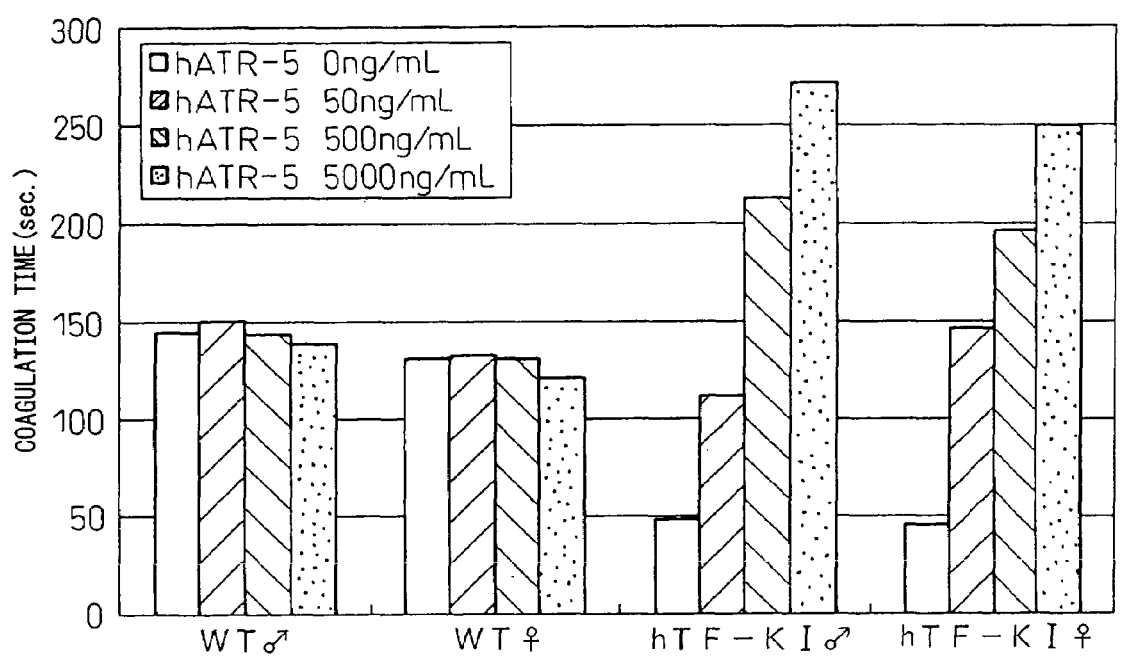
FIG. 6 is a graph similar to FIG. 5 but shows the result of determination of human plasma coagulation time.
Figure 7:
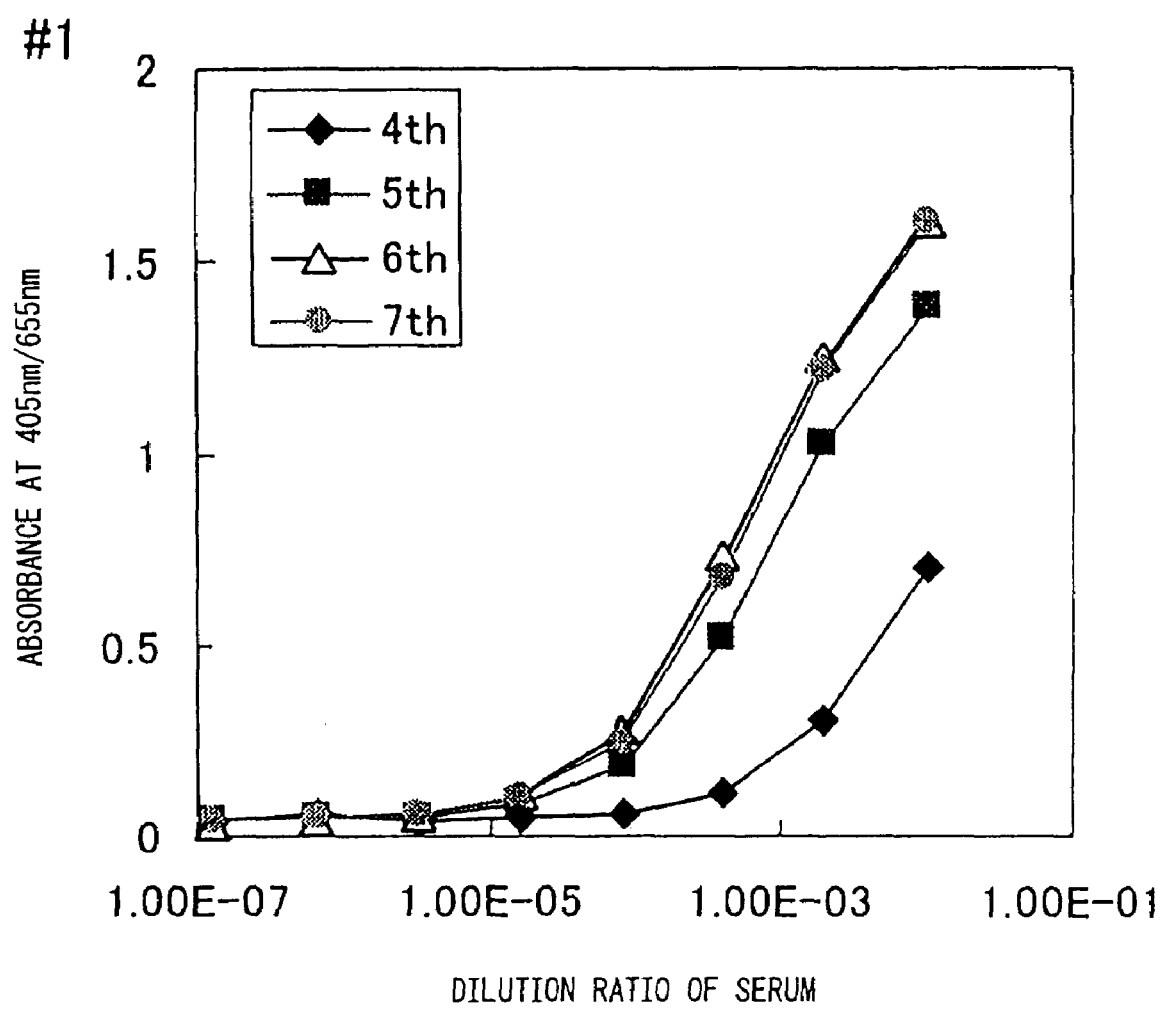
FIG. 7 is a graph showing a result of generation of anti-mouse TF antibody in Working Example 5, wherein the y-axis represents absorbance at 405 nm (reference 655 nm) and the x-axis represents the serum dilution factor. It shows the result of the 07 line mouse No. 1.
Figure 8:
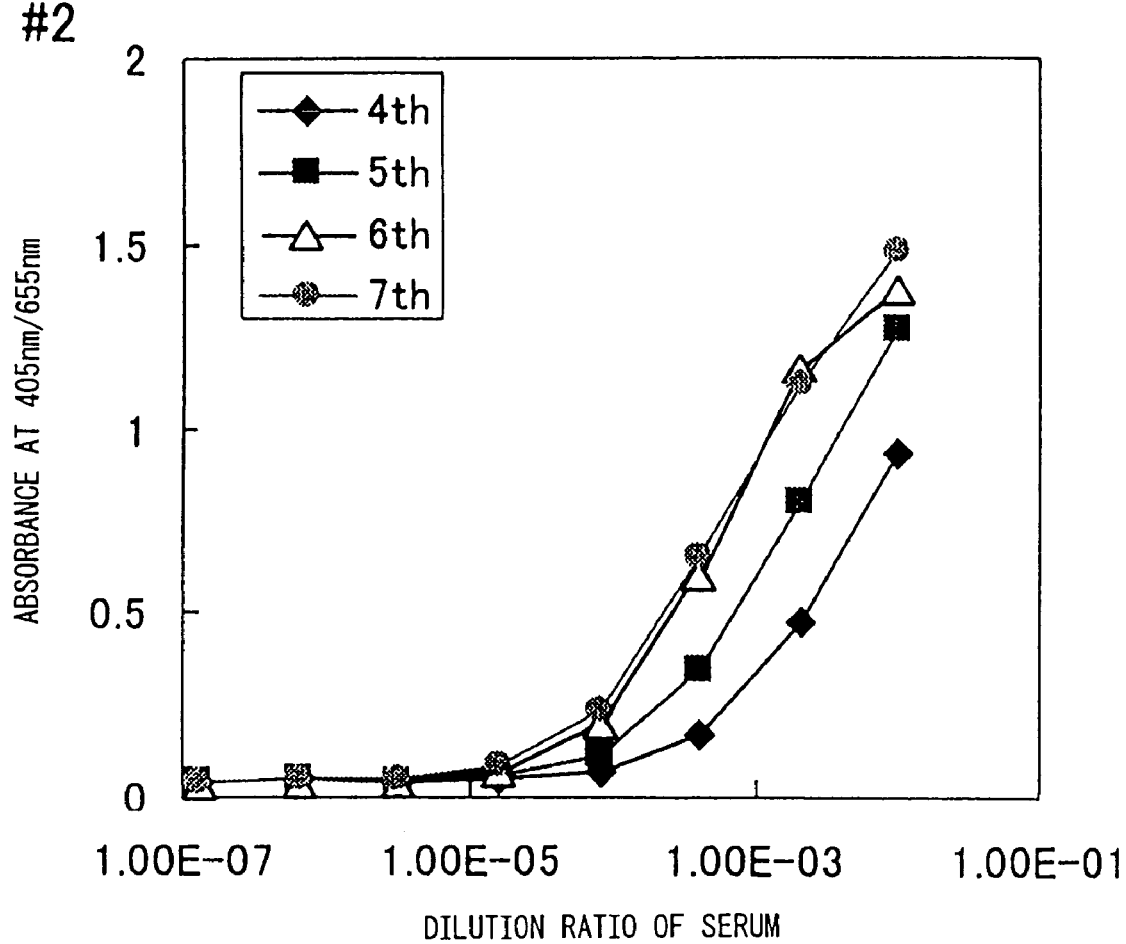
FIG. 8 is a graph similar to FIG. 7 showing the result of the 07 line mouse No. 2.
Figure 9:
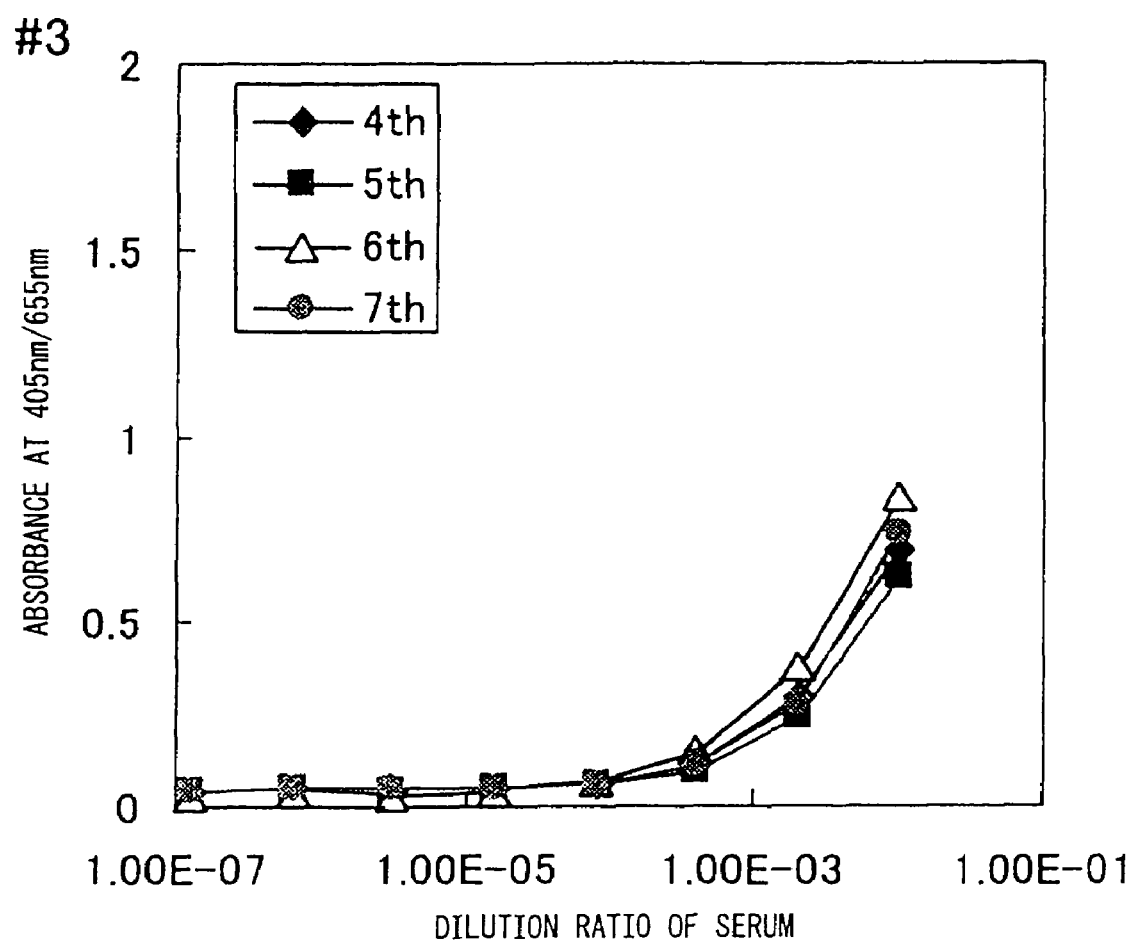
FIG. 9 is a graph similar to FIG. 7 showing the result of the 07 line mouse No. 3.

The results are shown in FIG. 5 and FIG. 6. FIG. 5 shows a result of mouse plasma coagulation time in which the y-axis represents plasma coagulation time, and each column represents the final concentration of the antibody. The coagulation activity of mouse plasma was detected at a similar degree in the wild type and the human TF knock-in mouse. With anti-human TF antibody, TF activity derived from the human TF knock-in mouse was only inhibited. FIG. 6 shows a result of human plasma coagulation time, in which the y-axis represents plasma coagulation time, and each column represents the final concentration of the antibody. The activity of wild type mouse TF was very weak compared to that of the human TF knock-in mouse (Janson T L. et al., (1984) Haemostasis 14:440-444). With anti-human TF antibody, TF activity derived from the human TF knock-in mouse was only inhibited.

EXAMPLE 3

Creation of Improved Knock-In Mice (1) Creation of Knock-In Mice

Mice in which the following two points have been improved compared to the mice created in Example 1 were established in a manner similar to Example 1.

Modification 1

The initiation codon ATG which is a protein translation initiation codon of the mouse TF gene was converted to CTG to introduce mutation in the mouse TF gene.

Modification 2

A sequence following the termination codon (codon TAA corresponding to 897-899 of SEQ ID NO: 7) of the human TF gene was modified to the sequence of 3' UTR of mouse TF.

The 3' UTR sequence of the mouse TF gene used is the 3' UTR region (from the base at position 989 to the last base (TAGAGGAAA-tgactccg, SEQ ID NO: 19)) of the sequence of the mouse genomic sequence described in Arteriosclerosis and Thrombosis 12(4):474 (1992)).

Specifically, using the genome of C57BL/6J mice as template, and the following PCR primers, PCR cloning was performed. PCR was performed in a reaction system of a total of 50 μl using 100 ng of template genomic DNA and TaKaRa LA Taq. The PCR condition was 95° C. for 1 minute, 35 cycles (95° C. for 0.5 min, 62° C. for 0.5 min, 72° C. for 1 min), and finally 72° C. for 7 minutes, and then reaction was terminated at 4° C.

```
FmTF3UTR:
5'-TCATCCTCCTGTCCATATCTCTGTGC-3'    (SEQ ID NO: 13)

RmTF3UTR:
5'-CGGAGTCACCTAATGTGAAAACCAAG-3'    (SEQ ID NO: 14)
```

The amplified fragment was subjected to TA cloning (Promega) to confirm the sequence, and was confirmed to be identical with the sequence described in the above article.

mTF 3' UTR of C57BL/6J mice obtained was added to the cording region of hTF (hTF CDS) by assemble PCR. To assemble PCR, Pyrobest (TaKaRa) was used.

Each of hTF cording region and mTF 3' UTR was amplified by PCR using primers hTFassem-mTFhTF, mTFassem-hT-FmTF (hTFassem: 5'-GGA TCC TCG AGG CCA CCA TGG AGA CCC CTG-3' (SEQ ID No. 15) (Xho I and BamHI sites were added), mTFassem: 5'-TCT AGA CTC GAG CGG AGT CAC CTA ATG TGA-3' (SEQ ID No. 16) (Xho I and Xba I sites were added), hTFmTF: 5'-ACT CCC CAC TGA ATG TTT CAT AAA GGA AAG GCT GAA GCG C-3' (SEQ ID No. 17), mTFhTF: 5'-GCG CTT CAG CCT TTC CTT TAT GAA ACA TTC AGT GGG GAG T-3' (SEQ ID No. 18), and the fragments obtained were purified. PCR was conducted at the condition of 95° C. for 1 minute, 30 cycles (95° C. for 0.5 min, 60° C. for 0.5 min, 72° C. for 1 min), 72° C. for 7 minutes and 4° C.

The purified hTF cording region and mTF 3' UTR fragment were mixed, and subjected to assemble PCR at the following condition. After two cycles (94° C. for 2 min, 58° C. for 2 min, 72° C. for 2 min) in the absence of primers, hTFassem and mTFassem primers were added, and 30 cycles (95° C. for 0.5 min, 58° C. for 0.5 min, 72° C. for 21 min), and finally a treatment of 72° C. for 7 minutes was carried out, and then reaction was terminated at 4° C.

Using the DNA obtained, a knock-in mouse was created in a manner similar to Example 1.

(2) Expression Analysis of hTF

In a manner similar to Example 1, the expression of TF in the brain was analyzed by Northern blot method.

For expression analysis, there were used those in which the human TF gene (knocked-in gene) is present in only one of the chromosomes and the other has been conserved (wild type) in both of the unimproved knock-in mice (the mouse in Example 1) and the improved knock-in mice. Accordingly, both of the unimproved knock-in mice and the improved knock-in mice express both of human TF and mouse TF.

Thus, when a human gene inserted into the mouse is highly expressed, the use of mouse 3' UTR instead of human 3' UTR is a very effective method.

This method is believed to be applicable not only to the mouse but also to the creation of other knock-in non-human animals, and by adding the 3' UTR derived from the knock-in non-human animal to the gene to be inserted, the inserted gene can be controlled to be expressed at a high level.

EXAMPLE 4

Arterial Occlusion Model

Using the human TF knock-in mouse the 76 line (♂, 8-20 week-old), an arterial thrombosis model was created. Mice were anesthetized with the administration of pentobarbital (50 mg/kg, i.p.), and the mice were retained at the dorsal position, and the rectal temperature measuring probe was mounted thereon. An incision was made in the neck to remove the left common carotid artery, from which nerves running in parallel with the artery were peeled to isolate the artery from the other tissues. A humanized anti-human TF antibody hATR-5 (ib2) (WO99/51743) (30 mg/kg) or the solvent therefor (20 mM sodium acetate buffer, pH 6.0, containing 150 mM NaCl) were intravenously given (50 µl/10 g B.W.) through the tail vein or the right common cervical vein. A soft cuff probe 0.5 mm, 20 MHz, (Crystal Biotech) connected to the Pulsed Doppler Flow/Dimension System, Model SAGE3 (Triton Technology, Inc.) was mounted to the artery, and monitored on the chart recorder LINEARCORDER mark VII WR3101 (Graphtec). After the passage of 5 minutes or more after the drug administration, a stimulus was given to the artery at the condition of rectal temperature of 36-37° C. A glycerin solution containing 40 w/v % $FeCl_3.6H_2O$ (FeG) was attached drop by drop to the surface of the blood vessel on the heart side from the probe mounting site of the common carotid artery for stimulation. After stimulation for 2 minutes, FeG was removed, and while monitoring the blood flow shown on the chart, the canalization of the artery was monitored. The observation lasted for 30 minutes after the start of stimulation, and the canalization time was determined and the patency rate was calculated.

The administration of hATR-5 (ib2) significantly prolonged the patency duration, and the patency rate increased significantly, and thus suppressed arterial obstruction significantly.

| Group | Patency duration (min) | Patency rate (%) |
|---|---|---|
| Solvent administration group (n = 19) | 15.7 ± 1.5 | 52.4 ± 5.1 |
| hATR-5 (ib2) administration group (n = 19) | 20.5 ± 1.2 | 68.4 ± 4.1 |
| P value | 0.020 | 0.020 |

EXAMPLE 5

Creation of Anti-Mouse TF Antibody Using the Human TF Knock-In Mice

Mouse TF was emulsified by mixing with an equal volume of Freund's complete adjuvant (Difco Laboratories) in a glass syringe. As mouse TF, CHO cell-derived soluble TF (smTF) was used. By subcutaneous injection of 10 µg/mouse, three mice each of male knock-in 07 line and 76 line were immunized. Two weeks later, smTF was emulsified by mixing with an equal amount of Freund's incomplete adjuvant (Difco Laboratories) (smTF-FIA) in a glass syringe, 10 µg/mouse of which was subcutaneously injected for immunization. Thereafter, smTF-FIA was subcutaneously given every week for immunization. 10 µg/mouse equivalent of smTF was injected for the second to fourth weeks, 30 µg/mouse equivalent for the fifth week, and 20 µg/mouse equivalent for the sixth and seventh weeks, for immunization.

Blood was taken from the orbit immediately before each immunization, serum was separated and the antibody titer of anti-mouse TF antibody was determined by ELISA. Blood drawing after the seventh immunization was performed four days after the immunization. The procedure for ELISA is shown below.

smTF was diluted to 1 µg/ml in the immobilization buffer, dispensed into a 96-well microwell plate (Maxisorp; Nunc) at 100 µl/well to immobilize smTF. As the immobilization buffer, sodium bicarbonate solution (pH 9.6) containing 0.02 w/v % $NaN_3$ was used. After washing three times with a wash buffer at 300 µl/well, it was blocked with a blocking buffer at 200 µl/well. The wash buffer used was PBS(−) containing 0.05 vol % of Tween™ 20, and the blocking buffer used was 50 mM Tris-HCl buffer (pH 8.1) containing 0.15 M NaCl, 1 mM $MgCl_2$, 0.05 vol % of Tween™ 20, 0.02 w/v % $NaN_3$, and 1 w/v % bovine serum albumin. After discarding the blocking buffer, antiserum diluted as appropriate with the blocking buffer was reacted at 100 µl/well (room temperature, 1 hour). After washing three times with the wash buffer at 300 µl/well, AP-Goat Anti-Mouse IgG (H+L) (ZYMED Laboratories) diluted 1,000-fold in the blocking buffer was reacted at 100 µl/well (room temperature, 2 hours). After washing five times with the wash buffer at 300 µl/well, an alkaline phosphatase substrate solution was dispensed at 100 µl/well to develop color at room temperature, absorbance was measured at 405 nm (reference 655 nm). Absorbance was measured using the Model 3550 Microplate Reader (Bio-Rad). The solution was 50 mM sodium bicarbonate solution (pH 9.8) containing 1 mg/ml SIGMA™ 104 and 10 mM $MgCl_2$.

As a result, antibody titer to mouse TF increased and antiserum was obtained.

The result are shown in FIGS. 7-12.

EXAMPLE 6

Creation of LPS-Induced DIC Model

Sepsis was induced by administering LPS to each of the wild type mouse and the human TF knock-in mouse. The wild type mouse used is C57BL/6J (CLEA Japan, Inc.), female, 15 weeks old, and the human TF knock-in mouse used is the 76 line, female, 14 weeks old. LPS used is derived from *Escherichia coli* (serotype 0111: B4) (SIGMA-Aldrich Co.). LPS was dissolved in physiological saline, and 0.5 mg/kg was given to the wild type mouse, and 0, 1, 5, 25 mg/kg was given to the hTF knock-in mouse intraperitoneally (0.1 ml/10 g B.W.). Six hours after the administration, blood was taken from the abdominal portion of vena under ether anesthesia. At this time, 3.8% citric acid was added to a final volume of 1/10 as an anticoagulant. Platelet count was measured using an automated blood cell counter F-800 (Sysmex).

Platelet count decreased confirming that the symptom of DIC developed.

| LPS dose | hTFKI mice | C57BL/6J mice |
|---|---|---|
| 0 mg/kg | 103.1 ± 19.3 (5) | 111.4 ± 5.1 (5) |
| 1 mg/kg | 80.1 ± 15.5 (5) | — |
| 5 mg/kg | 78.1 ± 12.1 (5) | 63.4 ± 8.5 (4) |
| 25 mg/kg | 70.6 ± 8.5 (4) | — |

( ) indicates the number of animals.

REFERENCE EXAMPLE 1

Creation of Anti-Mouse TF Antibody (1) Preparation of Antigen

A gene encoding the recombinant soluble mouse tissue factor protein (smTF) in which a sequence of amino acids 1-29 at the N terminal end of the amino acids 1-251 (Hartzell S. et al. (1989) Mol. Cell. Biol. 9:2567-2573) of mouse tissue factor (mouse TF) was replaced with methionine for *E. coli* expression and a FLAG peptide (DYKDDDDK, SEQ ID NO: 20) was added to the C terminal, and it was inserted into an *E.* coli expression vector containing T7 promoter, which was introduced into E. coli strain BL21.

IPTG at a final concentration of 1 mM was added to the culture of transformed E. coli to induce the expression of smTF, E. coli was collected, and the lysate was analyzed on SDS-PAGE with a result that smTF was expressed as a protein of molecular weight about 25 kDa. The transformed E. coli was cultured at 2 L, and when absorbance at 600 nm reached 0.2, IPTG was added at a final concentration of 1 mM, which was further cultured for 5 hours to harvest the cells. The cells collected were stored frozen at −80° C.

After the cells were disrupted by sonication, the precipitate after cell disruption was washed three times with 4% Triton X-100 and 2 M urea, was further washed twice with MilliQ water, and then was solubilized in 100 ml of 8 M urea/10 mM dithiothreitol/50 mM Tris-HCl buffer (pH 8.5). It was centrifuged at 25,000×G for 20 minutes to remove the insoluble substances and to recover soluble substances, which were designated as smTF(U). In order to allow the smTF(U) to refold, 50 ml of smTF(U) was dialyzed against 5 mM reduced glutathione/1 mM oxidized glutathione/20 mM Tris-HCl buffer (pH 7.4), and two hours and six hours later the dialysis external solution was changed for further dialysis for 16 hours.

A solution obtained by centrifuging the dialysis internal solution at 25,000×G for 20 minutes was desalted with 20 mM Tris-HCl buffer (pH 7.4) to remove glutathione, which was then added to the Resource Q6ml column (Pharmacia Biotech) equilibrated with 20 mM Tris-HCl buffer (pH 7.4), and washed in 2 column volumes of the same buffer. In the 20 mM Tris-HCl buffer (pH 7.4), NaCl concentration was linearly increased from 0 M to 0.3 M to elute soluble mouse TF. The soluble mouse TF fraction obtained was designated as smTF(R).

(2) Immunization and Preparation of Hybridoma

Recombinant soluble mouse tissue factor (TF) was emulsified (oil-in-water type) by mixing with an equal amount of Freund's complete adjuvant (Difco Laboratories) in a glass syringe for about 30 minutes. As TF, smTF(R) at 50 μg/rat and smTF(U) at 100 μg/rat were subcutaneously inoculated to the lamb of 6 week-old male Wistar rats (Nippon Charles River).

As a booster, Freund's incomplete adjuvant (Difco Laboratories) instead of Freund's complete adjuvant was used in a similar manner to prepare an emulsion, which was administered on day 15 and 22 after the initial immunization at 50 μg/rat for smTF(R) and at 100 μg/rat for smTF(U), and furthermore on day 29, 43, and 50 after the initial immunization, smTF(R) at 25 μg/rat and smTF(U) at 50 μg/rat were subcutaneously inoculated to the lamb of the rats. Using the immunogen described below as antigen in ELISA, a sufficient increase in antibody titer was confirmed, and then as a final immunization on day 57 after the initial immunization, smTF (R) at 50 μg/rat and smTF(U) at 100 μg/rat were administered via the tail vein.

Three days after the final immunization, spleen cells were aseptically prepared from the rats, and $1.85 \times 10^8$ spleen cells prepared and $1.85 \times 10^7$ mouse myeloma cells P3/X63-Ag8.U1 (hereinafter P3U1) were mixed, and the cells were fused according to a standard method (Harlow, E. and Lane, D. (1988) Antibodies A Laboratory Manual, Cold Spring Harbor Laboratory) using polyethylene glycol 1500 (BOEHRINGER MANNHEIM). The fused cells were suspended in a RPMI 1640 medium (GIBCO BRM) containing 10% bovine fetal serum (INTERGEN) (hereinafter RPMI medium), and plated to 96-well micro plate at a P3U1 density of $5 \times 10^4$ cells/100 μl/well, and cultured.

The number of 96-well micro plates onto which the cells are plated was four plates per rat (the number of wells, 352). On the next day, RPMI medium containing 2% BM-condimed H1 (BOEHRINGER MANNHEIM) and HAT (GIBCO BRL) (hereinafter, HAT medium) was added at 100 μl/well, and on day 2, 3, and 5 after cell fusion, the half amount was replaced with the HAT medium for HAT selection.

On day 9 after cell fusion, the antibody titer of each well was determined by cell ELISA as a primary screening. Cells from wells that exhibited high absorbance were subcultured to 12 well plates for a secondary screening.

Four days after the primary screening, as a secondary screening, antibody titer by cell ELISA and by ELISA using as antigen smTF(U) and smTF expressed in COS cells (smTF (cos)) and the inhibitory activity of Factor Xa production were determined. For the wells in which the inhibitory activity of both Factor Xa production and Factor X binding were observed, typing of antibodies were performed.

Hybridomas selected in the secondary screening were cloned by repeating twice limiting dilution, and conditioned in an RPMI 1640 medium containing 2% BM-codimed H1. After confirming productivity of antibody, this was considered to be the completion of establishment of hybridomas.

Finally, six clones of antibody (MFR-36, MFR-37, MFR-40, MFR-66 (IgG2a), MFR-25, MFR-51 (IgM)) having both of the inhibitory activity of human Factor Xa production and the inhibitory activity of human Factor X binding were established.

(3) Preparation of Ascites and Purification of Antibody

Preparation of ascites of the hybridoma established was carried out according to a standard method. Thus, $1 \times 10^6$ hybridoma (MFR-37) cells that had been subcultured in vitro were intraperitoneally transplanted to male BALB/c nude mouse, BALB/c-nu/nu (Japan Charles River) that had intraperitoneally received mineral oil twice. The ascites was recovered from the mouse that exhibited a bloated abdomen 1-2 weeks after the transplantation.

Purification of antibody (MFR-37) from the ascites was performed out using a combination of SP Sepharose Fast Flow column chromatography and Protein G Sepharose 6 FF column chromatography. Thus, it was diluted 10-fold with 20 mM sodium acetate buffer (pH 5.0), allowed to adsorb to a SP Sepharose Fast Flow column (50 mm ID×130 mmH), washed with 20 mM sodium acetate buffer (pH 5.0), and eluted in 20 mM sodium acetate buffer (pH 6.0) containing 500 mM sodium chloride. The eluted fraction was adjusted to about pH 6 with 1 M Tris solution, and was allowed to adsorb to a Protein G Sepharose 6 FF column (16 mm ID×125 mmH).

After washing with about 10 column volumes of 20 mM sodium acetate buffer (pH 6.0), it was eluted with 50 mM acetic acid. After the eluted fraction was diluted two-fold in distilled water, pH was adjusted to 5.0 with 1 M Tris solution, and was allowed to adsorb to an SP Sepharose XL column (10 mm ID×100 mmH). After washing with about 10 column volumes of 20 mM sodium acetate buffer (pH 5.0), it was eluted with 20 mM sodium acetate buffer (pH 6.0) containing 200 mM sodium chloride to prepare purified antibody.

REFERENCE EXAMPLE 2

Preparation of CHO Cell-Derived Soluble Mouse TF

A gene encoding protein in which a FLAG peptide (DYKDDDDK, SEQ ID NO: 20) was added to the C terminal of the amino acids No. 1-251 (Hartzell S. et al. (1989) Mol. Cell. Biol. 9: 2567-2573) of TF was inserted to an expression vector for mammals containing the DHFR expression gene, and introduced into CHO cells. Methotrexate was used to amplify expression and the soluble mouse TF-producing CHO cells were established.

The cells were cultured in a serum-free CHO-S-SFM II (GIBCO BRL) to obtain a culture supernatant containing soluble mouse TF. Two volumes of 20 mM Tris-HCl buffer (pH 8.5) were added to the culture supernatant, and diluted three-fold. It was added to a Q-Sepharose Fast Flow column (200 ml, Pharmacia Biotech) equilibrated with 20 mM Tris-HCl (pH 8.5), and washed with three column volumes of the same buffer. In 20 mM Tris-HCl buffer (pH 8.5), NaCl concentration was linearly increased from 0 M to 1 M to elute soluble mouse TF.

Ammonium sulfate was added to the soluble mouse TF thus obtained to a 30% saturation, and after centrifugation contaminating proteins were precipitated. The supernatant was recovered, to which ammonium sulfate was further added to a 50% saturation, and after centrifuge, contaminating proteins were precipitated. The supernatant was applied on Butyl-TOYOPEARL (21.5 ml, TOSOH), and washed with three column volumes of 50 mM Tris-HCl buffer (pH 6.8) containing 1.8 M ammonium sulfate. In 50 mM Tris-HCl buffer (pH 6.8), the ammonium sulfate concentration was linearly decreased from 1.8 M to 0 M to elute soluble mouse TF.

Peak fractions containing soluble mouse TF were concentrated by Centri-Prep 10 (Amicon). The concentrate was applied on the TSKgel G3000 SWG column (21.5×600 mm, TOSOH) equilibrated with 20 mM sodium phosphate buffer (pH 7.0) containing 150 mM NaCl, and the peak fraction of soluble mouse TF was collected. This was sterilized with a 0.22 μm membrane filter to prepare the CHO cell-derived soluble mouse TF. The concentration of the sample was calculated using the molar extinction coefficient of the sample of $\epsilon=39,670$ and molecular weight of 45,000.

The invention claimed is:

1. A human tissue factor (TF) homozygous mouse whose genome comprises a human tissue factor gene that has been inserted upstream of the translation initiation codon for the mouse TF gene and is operably linked to the endogenous mouse TF promoter, wherein the mouse produces human TF without producing mouse TF, and the transgene is inserted in a 129 SvEv C57B1/6J genetic background, and wherein the mouse exhibits a phenotype of a propagative ability similar to that of a wild type mouse, and inhibited blood coagulation activity by human TF upon administration of an anti-human TF antibody.

2. The human tissue factor homozygous mouse according to claim 1 wherein the human TF-encoding gene comprises an AU-rich response element (ARE) or a polyA additional signal at the 3'-end thereof.

3. The human tissue factor homozygous mouse according to claim 2 wherein the human TF-encoding gene comprises an AU-rich response element (ARE) and a polyA additional signal at the 3'-end thereof.

* * * * *

UNITED STATES PATENT AND TRADEMARK OFFICE
CERTIFICATE OF CORRECTION

PATENT NO. : 7,592,502 B2 Page 1 of 1
APPLICATION NO. : 10/478058
DATED : September 22, 2009
INVENTOR(S) : Habu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this

Twenty-first Day of September, 2010

David J. Kappos
*Director of the United States Patent and Trademark Office*

SEQUENCE LISTING

```
<160> NUMBER OF SEQ ID NOS: 20

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      primer mTF1SpS

<400> SEQUENCE: 1
cgagcaaatg ctactagtag gataagtgat cgtctaaggc                              40

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer mTF2A

<400> SEQUENCE: 2
ctgtacagtg taggtatagt tggtgggttt gggttg                                  36

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer mTFe6ScA

<400> SEQUENCE: 3
atcagagctc tccgcaacag tgccgt                                             26

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer ShTF3

<400> SEQUENCE: 4
tgttcaagca gtgattccc                                                     19
```

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic primer RhTF2

<400> SEQUENCE: 5
aacaattccc agtcacctt                                                    19

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
aataaaggtg actgggaatt gtt                                               23

<210> SEQ ID NO 7
<211> LENGTH: 2041
<212> TYPE: DNA
<213> ORGANISM: Homo sapiens
<220> FEATURE:
<223> OTHER INFORMATION: cDNA coding for human tissue factor

<400> SEQUENCE: 7

| | | | | | |
|---|---|---|---|---|---|
| aattggccac | catggagacc | cctgcctggc | ccgggtccc | gcgccccgag | accgccgtcg | 60 |
| ctcggacgct | cctgctcggc | tgggtcttcg | cccaggtggc | cggcgcttca | ggcactacaa | 120 |
| atactgtggc | agcatataat | ttaacttgga | aatcaactaa | tttcaagaca | attttggagt | 180 |
| gggaacccaa | acccgtcaat | caagtctaca | ctgttcaaat | aagcactaag | tcaggagatt | 240 |
| ggaaaagcaa | atgcttttac | acaacagaca | cagagtgtga | cctcaccgac | gagattgtga | 300 |
| aggatgtgaa | gcagacgtac | ttggcacggg | tcttctccta | cccggcaggg | aatgtggaga | 360 |
| gcaccggttc | tgctggggag | cctctgtatg | agaactcccc | agagttcaca | ccttacctgg | 420 |
| agacaaacct | cggacagcca | acaattcaga | gttttgaaca | ggtgggaaca | aaagtgaatg | 480 |
| tgaccgtaga | agatgaacgg | actttagtca | aaggaacaa | cactttccta | agcctccggg | 540 |
| atgttttttgg | caaggactta | atttatacac | tttattattg | gaaatcttca | agttcaggaa | 600 |
| agaaaacagc | caaaacaaac | actaatgagt | ttttgattga | tgtggataaa | ggagaaaact | 660 |
| actgtttcag | tgttcaagca | gtgattccct | cccgaacagt | taaccggaag | agtacagaca | 720 |
| gcccggtaga | gtgtatgggc | caggagaaag | gggaattcag | agaaatattc | tacatcattg | 780 |
| gagctgtggt | atttgtggtc | atcatccttg | tcatcatcct | ggctatatct | ctacacaagt | 840 |
| gtagaaaggc | aggagtgggg | cagagctgga | aggagaactc | cccactgaat | gtttcataaa | 900 |
| ggaagcactg | ttggagctac | tgcaaatgct | atattgcact | gtgaccgaga | acttttaaga | 960 |
| ggatagaata | catggaaacg | caaatgagta | tttcggagca | tgaagaccct | ggagttcaaa | 1020 |
| aaactcttga | tatgacctgt | tattaccatt | agcattctgg | ttttgacatc | agcattagtc | 1080 |
| actttgaaat | gtaacgaatg | gtactacaac | caattccaag | ttttaatttt | taacaccatg | 1140 |
| gcacctttg | cacataacat | gcttagatt | atatattccg | cacttaagga | ttaaccaggt | 1200 |
| cgtccaagca | aaaacaaatg | ggaaaatgtc | ttaaaaaatc | ctgggtggac | ttttgaaaag | 1260 |

```
cttttttttt ttttttttt tgagacggag tcttgctctg ttgcccaggc tggagtgcag    1320
tagcacgatc tcggctcact tgcaccctcc gtctctcggg ttcaagcaat tgtctgcctc    1380
agcctcccga gtagctggga ttacaggtgc gcactaccac gccaagctaa ttttgtatt    1440 ttttagtaga gatggggttt caccatcttg gccaggctgg tcttgaattc ctgacctcag    1500
tgatccaccc accttggcct cccaaagatg ctagtattat gggcgtgaac caccatgccc    1560
agccgaaaag cttttgaggg gctgacttca atccatgtag gaaagtaaaa tggaaggaaa    1620
ttgggtgcat ttctaggact tttctaacat atgtctataa tatagtgttt aggttctttt    1680 tttttcagg aatacatttg gaattcaaa acaattgggc aaactttgta ttaatgtgtt      1740
aagtgcagga gacattggta ttctgggcag cttcctaata tgctttacaa tctgcacttt    1800
aactgactta agtggcatta acatttgag agctaactat atttttataa gactactata    1860
caaactacag agtttatgat ttaaggtact taaagcttct atggttgaca ttgtatatat    1920
aattttttaa aaaggttttt ctatatgggg attttctatt tatgtaggta atattgttct    1980
atttgtatat attgagataa tttatttaat atactttaaa taaggtgac tgggaattgt     2040 t                                                                    2041

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      loxP nucleotide sequence

<400> SEQUENCE: 8
ataacttcgt atagcataca ttatacgaag ttat                                34

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer mTF2

<400> SEQUENCE: 9
ccagtaggat aagtgatcgt ctaaggc                                        27

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer hTF-A

<400> SEQUENCE: 10
gccacagtat ttgtagtgcc tgaagc                                         26

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer mTF-5

<400> SEQUENCE: 11
ttcactcaaa cccactgcgg                                                20
```

-continued

```
<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer mTF-H

<400> SEQUENCE: 12
gctacgctac aggagcgatc g                                            21

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer FmTF3UTR

<400> SEQUENCE: 13
tcatcctcct gtccatatct ctgtgc                                       26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer RmTF3UTR

<400> SEQUENCE: 14
cggagtcacc taatgtgaaa accaag                                       26

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer hTFassem

<400> SEQUENCE: 15
ggatcctcga ggccaccatg gagacccctg                                   30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer mTFassem

<400> SEQUENCE: 16
tctagactcg agcggagtca cctaatgtga                                   30

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer hTFmTF

<400> SEQUENCE: 17
actccccact gaatgtttca taaaggaaag gctgaagcgc                        40
```

```
<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer mTFhTF

<400> SEQUENCE: 18
gcgcttcagc ctttccttta tgaaacattc agtggggagt                              40

<210> SEQ ID NO 19
<211> LENGTH: 17
<212> TYPE: DNA
<213> ORGANISM: Mus musculus

<400> SEQUENCE: 19
tagaggaaat gactccg                                                       17

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Tyr Lys Asp Asp Asp Asp Lys
 1               5
```